US007851505B2

(12) United States Patent
Ternansky et al.

(10) Patent No.: US 7,851,505 B2
(45) Date of Patent: Dec. 14, 2010

(54) THIOTUNGSTATE ANALOGUES AND USES THEREOF

(75) Inventors: Robert J. Ternansky, San Diego, CA (US); Patricia L. Gladstone, San Diego, CA (US); Amy L. Allan, Encinitas, CA (US); Melissa L. P. Price, Cardiff, CA (US); Andrew Mazar, San Diego, CA (US)

(73) Assignee: Attenuon, LLC, San Diego, CA (US)

( * ) Notice: Subject to any disclaimer, the term of this patent is extended or adjusted under 35 U.S.C. 154(b) by 1091 days.

(21) Appl. No.: 10/857,321

(22) Filed: May 27, 2004

(65) Prior Publication Data

US 2006/0160805 A1 Jul. 20, 2006

Related U.S. Application Data

(60) Provisional application No. 60/473,937, filed on May 27, 2003.

(51) Int. Cl.
C07C 217/28 (2006.01)
C07C 217/08 (2006.01)
C07C 215/40 (2006.01)
C07C 67/02 (2006.01)
A61K 31/22 (2006.01)
A61K 31/14 (2006.01)

(52) U.S. Cl. ............... 514/546; 514/529; 514/547; 514/642; 560/1; 560/196; 560/250; 560/251; 560/253; 564/291; 564/293

(58) Field of Classification Search ............... 564/291, 564/293; 560/1, 196, 253, 250, 251; 514/529, 514/546, 547, 642
See application file for complete search history.

(56) References Cited

U.S. PATENT DOCUMENTS

| 3,845,770 | A | 11/1974 | Theeuwes et al. |
|---|---|---|---|
| 3,916,899 | A | 11/1975 | Theeuwes et al. |
| 4,430,443 | A | 2/1984 | Seiver |
| 4,765,539 | A | 8/1988 | Noakes et al. |
| 5,112,598 | A | 5/1992 | Biesalski |
| 5,556,611 | A | 9/1996 | Biesalski |
| 5,639,725 | A | 6/1997 | O'Reilly et al. |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | van der Linden et al. |
| 6,703,050 | B1 | 3/2004 | Brewer et al. |
| 7,189,865 | B2 | 3/2007 | Ternansky et al. |
| 2004/0259945 | A1 | 12/2004 | Brewer et al. |
| 2005/0058720 | A1 | 3/2005 | Brewer et al. |
| 2006/0148891 | A1 | 7/2006 | Ternansky et al. |

FOREIGN PATENT DOCUMENTS

| WO | WO 00/13712 | 3/2000 |
|---|---|---|
| WO | WO 2004/009034 A2 | 1/2004 |
| WO | WO 2004/009072 | 1/2004 |
| WO | WO 2005/082382 A1 | 9/2005 |

OTHER PUBLICATIONS

Adelman et al., 1983, "In Vitro Deletional Mutagenesis for Bacterial Production of the 20,000-Dalton Form of Human Pituitary Growth Hormone." DNA 2:183-193.
Bajou et al., 1998, "Absence of host plasminogen activator inhibitor 1 prevents cancer invasion and vascularization." Nat. Med. 4:923-928.
Bamba et al., 1979 "Release Mechanisms in Gel-forming Sustained Release Preparations." Int. J. Pharrn 2, 307.
Benjamin et al., 1999, "Selective ablation of immature blood vessels in established human tumors follows vascular endothelial growth factor withdrawal." J. Clin. Invest 103:159-165.
Blood et al., 1990, "Tumor interactions with the vasculature: angiogenesis and tumor metastasis." Biochem. Biophys, Acta. 1032: 89-118.
Borgstrom et al., 1998, "Neutralizing anti-vascular endothelial growth factor antibody completely inhibits angiogenesis and growth of human prostate carcinoma micro tumors in vivo." Prostrate 35:1-10.
Brem et al., 1990, "Anticopper treatment inhibits pseudopodial protrusion and the invasive spread of 9L gliosarcoma cells in the rat brain." Neurosurgery. 26:391-396.
Brem et al., 1990, "Inhibition of angiogenesis and tumor growth in the brain. Suppression of endothelial cell turnover by penicillamine and the depletion of copper, an angiogenic cofactor." Am. J. Pathol. 137(5):1121-1142.
Brown, 2001, "Copper and Prion disease." Brain Res. Bull 55:165-173.
Brown, 2002, "Copper and Prion disease." Biochem. Soc. Tras. 30:742-745.
Carri et al., 2001, "Copper-dependent oxidative stress, alteration of signal transduction and neurodegeneration in amyotrophic lateral sclerosis." Funct. Neurol. 16:181-188.
Chakravarty et al., 1984, "Serum copper in malignant neoplasia with special reference to the cervix uteri." J. Cancer Res. Clin. Oncol. 108:312-315.
Chambers et al., 1995, "Macrophage colony-stimulating factor mediates invasion of ovarian cancer cells through urokinase." Canc. Res. 55:1578-1585.

(Continued)

*Primary Examiner*—Peter G O'Sullivan
(74) *Attorney, Agent, or Firm*—Jones Day

(57) ABSTRACT

The current invention provides novel thiotungstate derivatives, methods of making novel thiotungstate derivatives, pharmaceutical compositions of novel thiotungstate derivatives, methods of using novel thiotungstate derivatives to treat diseases associated with aberrant vascularization, copper metabolism disorders and obesity and methods of using pharmaceutical compositions of thiotungstate derivatives to treat diseases associated with aberrant vascularization, copper metabolism disorders, neurodegenerative disorders, obesity or NF-κB dysregulation.

15 Claims, 1 Drawing Sheet

OTHER PUBLICATIONS

Figure 1:
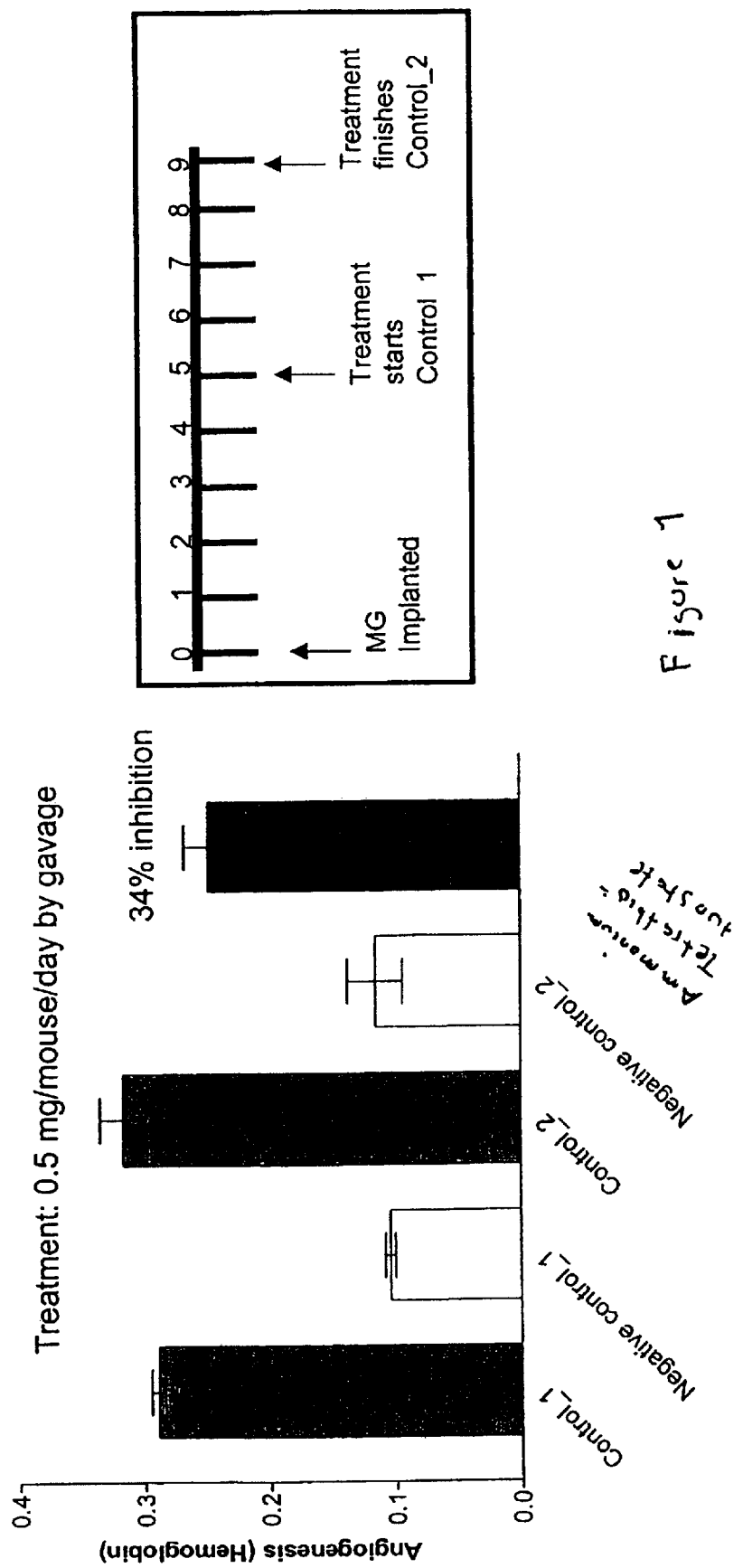

Chen et al., 2002, "TNF-R1 signaling: A beautiful Pathway." Science 296:1634-5.
Crowley et al., 1993, "Prevention of Metastasis by Inhibition of the Urokinase Receptor" Proc. Natl. Acad. Sci. USA 90: 5021-5025.
During et al., 1989, "Controlled Release of Dopamine from Polymeric Brain Implant: In Vivo Characterization." Ann. Neurol. 25:351.
Folkman, 1972, "Anti-angiogenesis: new concept for therapy of solid tumors." Ann. Surg. 175: 409-416.
Folkman, 1995, "Angiogenesis inhibitors generated by tumors." Mol. Med 1(2): 120-122.
Folkman, 1995, "The influence of angiogenesis research on management of patients with breast cancer." Breast Cancer Res. Treat. 36(2): 109-118.
Gnjec et al., 2002, "Transition metal chelator therapy—a potential treatment for Alzheimer's disease." Front. Biosci 7:1016-23.
Goodson, 1984, "Medical Applications of Controlled Release." vol. 2, Chapt. 6, 115-138.
Gorelik et al., 1980, "Control of lung metastasis progression in mice: role of growth kinetics of 3LL Lewis lung carcinoma and host immune reactivity." J. Nat'l. Canc. Inst. 65:1257-1264.
Gorelik et al., 1980, "Host's immune state and kinetics of local tumor growth control—progression of postoperative lung metastasis." Rec. Results Canc. Res. 75:20-28.
Gullino, 1986, "Considerations on the mechanism of the angiogenic response." Anticancer Res. 6(2):153-158.
Hanada et al., 2002, "Regulation of cytokine signaling and inflammation." Cytokine Growth Factor Rev. 13:413-421.
Hanahan et al., 1996, "Patterns and emerging mechanisms of the angiogenic switch during tumorigenesis." Cell 86(3): 353-364.
Harrison et al., 1971-1996, "Compendium of Synthetic Organic Methods." vols. 1-8 John Wiley & Sons.
Hilgard et al., 1977, "Oral anticoagulation in the treatment of a spontaneously metastasising murine tumour (3LL)", Br. J. Cancer 35:78-86.
Howard et al., 1989, "Intercerebral Drug Delivery in Rats with Lesion-Induced Memory Deficit." J. Neurosurg., 71:105.
Isakov et al., 1982, "An immune response against the alloantigens fo the 3LL Lewis lung carcinoma prevents the growth of lung metastases, but not of local allografts." Invasion Metas. 2:12-32.
Kleinman et al., 1986, "Basement membrane complexes with biological activity." Biochemistry, 25: 312-318.
Koch et al., 1992, "Interleukin-8 as a macrophage-derived mediator of angiogenesis." Science 258:1798-801.
Kowalik-Jankowska et al., 2002, "Possible involvement of copper(II) in Alzheimer disease." Environ Health Perspect 5:869-870.
Langer, "New methods of drug delivery." Science 1990, 249:1527-1533.
Levy et al., 1985, "Inhibition of calcification of bioprosthetic heart valves by local controlled-release diphosphonate." Science 228: 190.
Llanos et al., 2002, "The molecular basis of copper homeostasis copper-related disorders." DNA Cell Biol. 21:259-270.
Loskutoff et al., 2000, "The fat Mouse: A powerful Genetic Model to Study Hemostatit Gene Expression in Obesity/NIDDM." Ann. N.Y. Acad Sci. 902:272-281.
Malave et al., 1979, "Influence of inoculation site on development of the Lewis lung carcinoma and suppressor cell activity in syngeneic mice." J. Nat'l. Canc. Inst. 62:83-88.
Maynard et al., 2002, "Overexpression of Alzheimer's Disease Amyloid-β Opposes the Age-dependent Elevations of Brain Copper and Iron." J. Biol. Chem 277: 44670-44676.
McDonald et al, 1983, "Syntheses and characterization of ammonium and tetraalkylammonium thiomolybdates and thiotungstates." Inorg Chim. Acta 72:205-210.
Merajver et al., 1998, "Cooper Depletion as and Anti-Angiogenic Strategy in HER2-neu Transgenic." Proceedings of Special AACR Conference on,Angiogenesis and Cancer, Abstract #B-11, Jan. 22-24.
Millauer et al., 1996, "Dominant-negative inhibition of Flk-1 suppresses the growth of many tumor types in vivo." Cancer Res. 56: 1615-1620.
Min et al., 1996, "Urokinase receptor antagonists inhibit angiogenesis and primary tumor growth in syngeneic mice." Cancer Res. 56: 2428-2433.
Miyake et al., 2000, "Transforming growth factor-beta1 stimulates contraction of human glioblastoma cell-mediated collagen lattice through enhanced alpha2 integrin expression." J. Neuropathol. Exp. Neurol. 59:18-28.
Nguyen et al., 1994, "Quantitation of angiogenesis and antiangiogenesis in the chick embryo chorioallantoic membrane." Microvascular Res. 47:31 40.
Odedra et al., 1991, "Low molecular weight angiogenesis factors." Pharmac. Ther. 49:111-124.
Osawa et al., 2002,, "Tumor Necrosis Factor Alpha-Induced Interleukin-8 Production via NF—kappaB and Phosphatidylinositol 30 Kinase/Akt Pathways Inhibits Cell Apoptosis in Human Hepatocytes." Infect Immun 70:6294-6301.
Pan et al., 2002, "Copper Deficiency Induced by Tetrathiomolybdate Suppresses Tumor Growth and Angiogenesis." Cancer Res. 62:4854-4859.
Parish et al., 1992, "A basement-membrane permeability assay which correlates with the metastatic potential of tumor cells." Int. J. Cancer 52:378-383.
Parke et al., 1988, "Characterization and Quantification of Copper sulfate-induced vascularization of the rabbit cornea." Am J. Pathol. 130:170-178.
Passaniti et al., 1992, A simple, quantitative method for assessing angiogenesis and antiangiogenic agents using reconstituted basement membrane, heparin, and fibroblast growth factor. Lab Invest. 67:519-528.
Perry et al., 2002, "The role of iron and copper in the aetiology of neurodegenerative disorders therapeutic implications." CNS Drugs 16:339-352.
Raju et al., 1982, "Ceruloplasmin, copper ions, and angiogenesis." Natl. Cancer. Inst. 69:1183-1188.
Rupnick et al., 2002, "From the cover: Adipose tissue mass can be regulated through the vasculature." Proc. Natl. Acad. Sci. 99:10730-10735.
Saudek et al., 1989, "A preliminary trial of the programmable implantable medication system for insulin delivery." N. Engl. J Med. 321:574-579.
Schnaper et al., 1995, "Plasminogen activators augment endothelial cell organization in vitro by two distinct pathways." J. Cell Physiol. 165:107-118.
Sefton, 1987, "Implantable pumps." CRC Crit. Ref. Biomed. Eng. 1987, 14:201-240.
Shockley et al., 1991, "Penetration of Tumor Tissue by Antibodies and Other Immunoproteins." Ann. N.Y. Acad. Sci. 617:367-382.
Strausak et al., 2001," Copper in disorders with neurological symptoms: Alzheirmer's Menkes, and Wilson disease."Brain Res. Bull 55:175-185.
Takai et al., 1996, Preparation, Structure, and Properties of Mixed-Metal Trinuclear-Complex: $(Pr_4N)_2[MoO(WS_4)_2]$ Chem. Letts. 645-646.
Talmadge et al., 1982, "Enhanced Metastatic Potential of Tumor Cells Harvested from Spontaneous Metastases of Heterogeneous Murine Tumors." J. Nat'l. Canc. Inst. 69:975-980.
Thakur et al., 1977, "Indium-111-labeled leukocytes for the localization of abscesses: preparation, analysis, tissue distribution, and comparison with gallium-67 citrate in dogs." J. Lab. Clin. Med. 89:217-228.
Treat et al., 1989, "Liposomes in the Therapy of Infectious Disease and Cancer." Lopez Berestein and Fidler (eds.), Liss, New York, pp. 353 365.
Verma et al., 2000, "Osmotically Controlled Oral Drug Delivery." Drug Dev. Ind. Pharm. 26:695-708.
Verschoyle et al., 1999, "Pharmacokinetics of Isotretinoin (ISO) in Rats following Oral Dosing or Aerosol Inhalation." Br. J. Cancer 80 Suppl. 2: 96.
Volpert et al., 1996, "Captopril Inhibits Angiogenesis and Slows the Growth of Experimental Tumors in Rats." J. Clin. Invest. 98: 671-679.
Xing et al., 1996, "Overexpression of Urokinase Receptor in Breast." Int. J. Cancer 1996, 67: 423-429.

Yoshida et al., 1995, "Copper chelation inhibits tumor angiogenesis in the experimental 9L gliosarcoma model." Neurosurgery 37(2):287-295.

Ziche et al., 1982, "Role of prostaglandin E1 and copper in angiogenesis." Natl. Cancer. Inst. 69:475-482.

Alonso, G., 2001, "Synthesis of tetraalkylammonium thiometallates in aqueous solution" Inorganica Chimica acta, vol. 325, pp. 193-197.

Bartecki, A., 1973, "Tetrahedral sulfur-containing molybdenum(VI) and tungsten(VI) chromophores" Inorganica Chimica Acta, vol. 7, No. 4, pp. 610-612.

Chandrasekaran, Jayanthi et al., 1988, "Synthesis and characterization of .mu.-sulfidodisulfidotetrakis(.eta 2-disulfido)dimolybdate (2-) and rational synthesis of [M2(L)2(.mu.-S)(.eta.2-S2)412-, (M = Mo, W; L = 0, S) anions" Inorganic Chemistry, vol. 27, pp. 3663-3665.

Dembicka, Danuta, 1975, "Thiomolybdates of some organic bases", Roczniki Chemii, vol. 49, No. 9, pp. 1475-1483.

Jin, Guoxin, 1987, "Synthesis, properties and substitution reactions of thiomolybdate and thiotungstate" Coord. Chem. Inst., vol. 3, No. 4, pp. 106-112.

Ramesha, A. R., 1992, "Benzyltriethylammonium tetrathiomolybdate:an improved sulfur transfer reagent for the synthesis of disulfides" Synthetic Communications, vol. 22, No. 22, pp. 3277-3284.

Udupa, M. R., 1975, "Piperidinium and pyrrolidinium tetrathiomolybdates and tetrathiotungstates" Current Science, vol. 44, No. 9, pp. 304-306.

Udupa, M. R., 1976, "Diethylammonium molybdates and tungstates" Journal of the Indian Chemical Society, vol. 53, No. 1, pp. 43-45, India.

Udupa, M. R., 1976, "Ethylenediammonium molybdates and tungstate", Journal of the Indian Chemical Society, vol. 53. No. 4. pp. 340-342. India.

Udupa, M. R., 1976, "Morpholinium molybdates and tungstates", Indian Journal of Chemistry, Section A, vol. 14A, No. 3, pp. 164-165, India.

Udupa, M. R., 1976, "N-Ethylmorpholinium molybdates and tungstates" Indian Journal of Chemistry, Section A, vol. 14A, No. 7. pp. 529-530, India.

Zaitsev. V. P.. 1996, "Behavior of molybdenum thio complexes in extraction systems with quaternary ammonium salts" Zhurnal Neorganicheskoi Khimii. vol. 41. No. 3, pp. 524-528. Moscow; RU. Supplemental Search Report from European Patent Application No. 03765973.7, dated May 23, 2008.

Alonso, G. et al., "Synthesis and Characterization of Tetraalkylammonium Thiomolybdates and Thiotungstates in Aqueous Solution," *Inorganica Chimica Acta*, 1998, vol. 274, No. 1, p. 108-110.

Fuchs, J. et al., "A novel preparation of thio- and thioxotungstates," *Zeitschrift fuer Naturforschung, Teil B: Anorganische Chemie, Organische Chemie, Biochemie, Biophysik, Biologie*, 1973, vol. 28, No. 11-12, p. 736-737.

Cohen, S. A. et al., "Dinuclear Tungsten(V) and Molybdenum(V) Compounds Containing $M_2S_2(\mu\text{-}S)_2^{2+}$ Cores. Synthesis and Reactivity of $[N(C_2H_5)_4]_2M_2S_{12}$ (M = W or Mo) and the Crystal Structure of $[N(C_2H_5)_4]_2W_2S_2(\mu\text{-}S)_2(S_4)_2$", *Inorganic Chemistry*, 1985, vol. 24, No. 26, p. 4657-4662.

Young, B.W. et al., "Effects of tetrathiotungstate and dithiotungstate on copper metabolism in rats", *Journal of Inorganic Biochemistry*, 1982, vol. 16, No. 2, p. 121-134.

THIOTUNGSTATE ANALOGUES AND USES THEREOF

1. FIELD

The present invention relates generally to tetrathiotungstate derivatives, methods of making novel tetrathiotungstate derivatives, pharmaceutical compositions of novel tetrathiotungstate derivatives, methods of using novel tetrathiotungstate derivatives and pharmaceutical compositions of tetrathiotungstate derivatives to treat or prevent diseases associated with aberrant vascularization, copper metabolism disorders, neurodegenerative disorders and obesity.

2. BACKGROUND

Most forms of cancer are derived from solid tumors (Shockley et al., *Ann. N.Y. Acad. Sci.* 1991, 617: 367-382, which have proven resistant in the clinic to therapies such as the use of monoclonal antibodies and immunotoxins. Anti-angiogenic therapy for the treatment of cancer was developed from the recognition that solid tumors require angiogenesis (i.e., new blood vessel formation) for sustained growth (Folkman, *Ann. Surg.* 1972, 175: 409-416; Folkman, *Mol. Med.* 1995, 1(2): 120-122; Folkman, *Breast Cancer Res. Treat.* 1995, 36(2): 109-118; Hanahan et al., *Cell* 1996, 86(3): 353-364). Efficacy of anti-angiogenic therapy in animal models has been demonstrated (Millauer et al., *Cancer Res.* 1996, 56:1615-1620; Borgstrom et al., *Prostrate* 1998, 35:1-10; Benjamin et al., *J. Clin. Invest.* 1999, 103: 159-165; Merajver et al., *Proceedings of Special AACR Conference on Angiogenesis and Cancer* 1998, Abstract #B-11, January 22-24). In the absence of angiogenesis, internal cell layers of solid tumors are inadequately nourished. Further, angiogenesis (i.e., aberrant vascularization) has been implicated in numerous other diseases (e.g., ocular neovascular disease, macular degeneration, rheumatoid arthritis, etc.). More recently, angiogenesis inhibition has been directly correlated with adipose tissue loss and weight loss in animal models, which suggests anti-angiogenic therapy may be useful in prevention of obesity (Rupnick et al., *Proc. Natl. Acad. Sci.* 2002, 99:10730-10735).

Contrastingly, normal tissue does not require angiogenesis except under specialized circumstances (e.g., wound repair, proliferation of the internal lining of the uterus during the menstrual cycle, etc.). Accordingly, a requirement for angiogenesis is a significant difference between tumor cells and normal tissue. Importantly, the dependency of tumor cells on angiogenesis, when compared to normal cells, is quantitatively greater than differences in cell replication and cell death, between normal tissue and tumor tissue, which are often exploited in cancer therapy.

Angiogenesis requires copper, as has been shown by numerous studies (Parke et al., *Am. J. Pathol.* 1988, 137:173-178; Raju et al., *Natl. Cancer Inst.* 1982, 69: 1183-1188; Ziche et al., *Natl. Cancer Inst.* 1982, 69: 475-482; Gullino, *Anticancer Res.* 1986, 6(2): 153-158). Attempts at preventing angiogenesis and hence tumor growth in animal models by reducing in vivo amounts of copper have been reported in the art (Brem et al., *Neurosurgery* 1990, 26:391-396; Brem et al., *Am. J. Pathol.* 1990, 137(5): 1121-1142; Yoshida et al., *Neurosurgery* 1995 37(2): 287-295). These approaches incorporated both copper chelators and low copper diets. More recently, Brewer et al., International Application No. PCT/US99/20374 have shown that the copper chelators, (e.g., tetrathiomolybdate) may be effective in treating diseases (e.g., solid tumor growth), which require angiogenesis.

In addition to the induction of angiogenesis, copper may also have a direct role in tumor cell growth and survival. High copper levels exist in both the plasma and in tumor tissue from patients with many different solid cancers (Chakravarty et al., *J Cancer Res. Clin. Oncol.* 1984, 108: 312-315). Recently, tetrathiomolybdate has been shown to down-regulate the expression of NF-κB as well as inhibit its translocation to the nucleus in the inflammatory breast cancer cell line SUM 149 (Pan et al., *Cancer Res.* 2002, 62: 4854-4859). The NF-κB system may be involved in mediating tumor cell survival and thus its down-regulation in tumor cells by tetrathiomolybdate suggests a direct effect of copper chelation on tumor survival.

Accordingly, novel compounds such as tetrathiotungstate compounds, which are copper chelators, are required to fully explore the potential of copper chelators in treating and/or preventing angiogenesis and in tumor cell viability. Such novel tetrathiotungstate compounds may be effective in treating various diseases associated with angiogenesis such as cancer and obesity along with copper metabolism disorders neurodegenerative disorders, obesity as well as treating diseases where the NF-κB pathway is dysregulated such as inflammatory disorders.

3. SUMMARY

The present invention satisfies this and other needs by providing novel tetrathiotungstate derivatives, methods of making novel tetrathiotungstate derivatives, pharmaceutical compositions of novel tetrathiotungstate derivatives, methods of using novel tetrathiotungstate derivatives to treat diseases associated with aberrant vascularization, copper metabolism disorders, neurodegenerative disorders and obesity and methods of using pharmaceutical compositions of tetrathiotungstate derivatives to treat or prevent diseases associated with aberrant vascularization, copper metabolism disorders, neurodegenerative disorders, obesity or NF-κB dysregulation.

In a first aspect, the present invention provides a compound of structural formula (I):

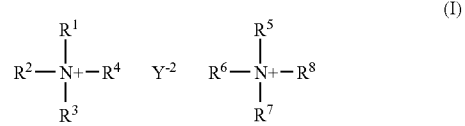

or a solvate, hydrate or N-oxide thereof wherein:
$R^1$, $R^2$, $R^3$, $R^5$, $R^6$ and $R^7$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl;
$R^4$ and $R^8$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or are absent when N is part of an aromatic ring;
optionally, $R^1$ and $R^2$ taken together are alkyldiyl, substituted alkyldiyl, heteroalkyldiyl or substituted heteroalkyldiyl;
optionally, $R^5$ and $R^6$ taken together are alkyldiyl, substituted alkyldiyl, heteroalkyldiyl or substituted heteroalkyldiyl;
optionally, $R^1$ and $R^2$ taken together, $R^2$ and $R^3$ taken together and $R^2$ and $R^4$ taken together are alkyldiyl, substituted alkyldiyl, heteroalkyldiyl or substituted heteroalkyldiyl;

optionally, $R^5$ and $R^6$ taken together, $R^6$ and $R^7$ taken together and $R^6$ and $R^8$ taken together are alkyldiyl, substituted alkyldiyl, heteroalkyldiyl or substituted heteroalkyldiyl;

optionally, $R^3$ and $R^7$ taken together are alkyldiyl, substituted alkyldiyl, heteroalkyldiyl or substituted heteroalkyldiyl; and $Y^{-2}$ is $(WS_4)^{-2}$, $(W_2S_{12})^{-2}$, $(W_2S_9)^{-2}$, $(W_2S_7)^{-2}$, $(W_2S_8)^{-2}$, $(W_2S_{11})^{-2}$, $(W_2S_6)^{-2}$ or $(W_2S_{13})^{-2}$.

In a second aspect, the present invention provides pharmaceutical compositions of compounds of the invention. The pharmaceutical compositions generally comprise one or more compounds of the invention, hydrates or solvates thereof and a pharmaceutically acceptable diluent, carrier, excipient and adjuvant.

The choice of diluent, carrier, excipient and adjuvant will depend upon, among other factors, the desired mode of administration.

In a third aspect, the present invention provides methods for treating or preventing diseases or disorders characterized by aberrant vascularization, copper metabolism disorders, neurodegenerative disorders, obesity or NF-κB dysregulation.

The methods generally involve administering to a patient in need of such treatment or prevention a therapeutically effective amount of a compound and/or pharmaceutical composition of the invention.

In a fourth aspect, the current invention provides pharmaceutical compositions for treating or preventing diseases or disorders characterized by aberrant vascularization, copper metabolism disorders neurodegenerative disorders, obesity or NF-κB dysregulation in a patient in need of such treatment or prevention.

4. BRIEF DESCRIPTION OF THE DRAWINGS

FIG. 1 illustrates inhibition of angiogenesis by ammonium tetrathiotungstate in Matrigel® plug assay.

5. DETAILED DESCRIPTION

5.1 Definitions

"Compounds" refers to compounds encompassed by structural formula (I) disclosed herein and includes any specific compounds within that generic formula whose structure is disclosed herein. Compounds may be identified either by chemical structure and/or chemical name. When the chemical structure and chemical name conflict, the chemical structure is determinative of the identity of the compound. Compounds may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. Compounds may also exist in several tautomeric forms including the enol form, the keto form and mixtures thereof. Accordingly, the chemical structures depicted herein encompass all possible tautomeric forms of the illustrated compounds. Compounds also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$, $^{17}O$ and $^{35}S$. Compounds may exist in unsolvated forms as well as solvated forms, including hydrated forms and as N-oxides. In general, the hydrated, solvated forms and N-oxides are within the scope of the present invention. Certain compounds may exist in multiple crystalline or amorphous forms. In general, all physical forms are equivalent for the uses contemplated herein. Further, it should be understood, when partial structures of the compounds are illustrated, that brackets indicate the point of attachment of the partial structure to the rest of the molecule.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, most preferably, from 1 to 6 carbon atoms.

"Alkanyl" by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl(isopropyl), cyclopropan-1-yl, etc.; butanyls such as butan-1-yl, butan-2-yl(sec-butyl), 2-methyl-propan-1-yl(isobutyl), 2-methyl-propan-2-yl (t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-y but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Preferably, the alkyldiyl group is ($C_1$-$C_{20}$) alkyldiyl, more preferably, ($C_1$-$C_{10}$) alkyldiyl, most preferably, ($C_1$-$C_6$) alkyldiyl. Preferred are saturated acyclic alkanyldiyl groups in which the radical centers are at the terminal carbons, e.g., methandiyl (methano); ethan-1,2-diyl (ethano); propan-1,3-diyl(propano); butan-1,4-diyl(butano); and the like (also referred to as alkyleno, defined infra).

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3] dieno, but[1]yno, but[2]yno, but[1,3]diyno, etc.; and the like. Where specific levels of saturation are intended, the nomenclature alkano, alkeno and/or alkyno is used. Preferably, the alkyleno group is ($C_1$-$C_{20}$) alkyleno, more preferably, ($C_1$-$C_{10}$) alkyleno, most preferably, ($C_1$-$C_6$) alkyleno. Preferred are straight-chain saturated alkano groups, e.g., methano, ethano, propano, butano, and the like.

"Acyl" by itself or as part of another substituent, refers to a radical —C(O)$R^{30}$, where $R^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" by itself or as part of another substituent, refers to a radical —$NR^{31}C(O)R^{32}$, where $R^{31}$ and $R^{32}$ are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino, cyclohexylcarbonylamino, cyclohexylmethyl-carbonylamino, benzoylamino, benzylcarbonylamino and the like.

"Alkoxy" by itself or as part of another substituent, refers to a radical —$OR^{33}$ where $R^{33}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent, refers to a radical —C(O)$OR^{33}$ where $R^{33}$ is as defined above.

"Aryl" by itself or as part of another substituent, refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably, from 6 to 12 carbon atoms.

"Arylalkyl" by itself or as part of another substituent, refers to an acyclic alkyl radical in which one of the hydrogen atoms bonded to a carbon atom, typically a terminal or $sp^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$-$C_{30}$) arylalkyl, e.g., the alkanyl, alkenyl or alkynyl moiety of the arylalkyl group is ($C_1$-$C_{10}$) and the aryl moiety is ($C_6$-$C_{20}$), more preferably, an arylalkyl group is ($C_6$-$C_{20}$) arylalkyl, e.g., the alkanyl, alkenyl or alkynyl moiety of the arylalkyl group is ($C_1$-$C_8$) and the aryl moiety is ($C_6$-$C_{12}$).

"Cycloalkyl" by itself or as part of another substituent, refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is ($C_3$-$C_{10}$) cycloalkyl, more preferably, ($C_3$-$C_7$) cycloalkyl.

"Cycloheteroalkyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl, Heteroalkanyl, Heteroalkyldiyl and Heteroalkyleno" by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —NR$^{35}$R$^{36}$—, =N—N=, —N=N—, —N=N—N$^{37}$R$^{38}$, —PR$^{39}$—, —P(O)$_2$—, —POR$^{39}$—, —O—P(O)$_2$—, —SO—, —SO$_2$—, —SnR$^{41}$R$^{42}$— and the like, where R$^{35}$, R$^{36}$, R$^{37}$, R$^{38}$, R$^{39}$, R$^{40}$, R$^{41}$ and R$^{42}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5-20 membered heteroaryl, more preferably from 5-10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl, more preferably, 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Parent Aromatic Ring System" by itself or as part of another substituent, refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutical composition" refers to at least one compound of the invention and a pharmaceutically acceptable vehicle, with which the compound is administered to a patient.

"Pharmaceutically acceptable salt" refers to a salt of a compound of the invention, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, prqpionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted to, for example, to a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, $2^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR60R^{61}$ where M is independently a halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. Preferably, substituents include -M, —$R^{60}$, =O, —$OR_{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$, more preferably, -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$, most preferably, -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

5.2 Compounds of Structural Formula (I)

In a first embodiment, the compounds of the invention include compound of structural formula (I):

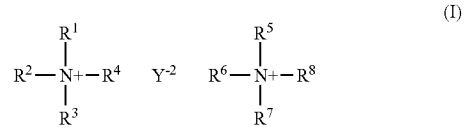

or a solvate or hydrate or N-oxide thereof wherein:

$R^1$, $R^2$, $R^3$, $R^4$, $R^6$ and $R^7$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl;

$R^4$ and $R^8$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or are absent when N is part of an aromatic ring;

optionally, $R^1$ and $R^2$ taken together are alkyldiyl, substituted alkyldiyl, heteroalkyldiyl or substituted heteroalkyldiyl;

optionally, $R^5$ and $R^6$ taken together are alkyldiyl, substituted alkyldiyl, heteroalkyldiyl or substituted heteroalkyldiyl;

optionally, $R^1$ and $R^2$ taken together, $R^2$ and $R^3$ taken together and $R^2$ and $R^4$ taken together are alkyldiyl, substituted alkyldiyl, heteroalkyldiyl or substituted heteroalkyldiyl;

optionally, $R^5$ and $R^6$ taken together, $R^6$ and $R^7$ taken together and $R^6$ and $R^8$ taken together are alkyldiyl, substituted alkyldiyl, heteroalkyldiyl or substituted heteroalkyldiyl;

optionally, $R^3$ and $R^7$ taken together are alkyldiyl, substituted alkyldiyl, heteroalkyldiyl or substituted heteroalkyldiyl; and $Y^{-2}$ is $(WS_4)^{-2}$, $(W_2S_{12})^{-2}$, $(W_2S_9)^{-2}$, $(W_2S_7)^{-2}$, $(W_2S_8)^{-2}$, $(W_2S_{11})^{-2}$, $(W_2S_6)^{-2}$ or $(W_2S_{13})^{-2}$.

In some embodiment, Y is $(WS_4)^{-2}$ and all of $R^1$, $R^2$, $R^3$, $R^4$, $R^5$, $R^6$, $R^7$ and $R^8$ are not hydrogen. In other embodiments, Y is $(WS_4)^{-2}$ and all of $R^1$, $R^2$, $R^3$, $R^4$, $R^5$, $R^6$, $R^7$ and $R^8$ are not alkyl.

In still other embodiments,

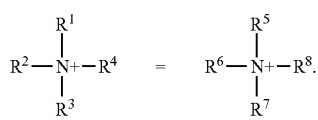

Preferably, Y is $(WS_4)^{-2}$.

In some embodiments, at least one of $R^1$, $R^2$, $R^3$ and $R^4$ is not alkyl. In other embodiments, $R^1$, $R^2$ and $R^4$ are hydrogen, alkanyl or substituted alkanyl. Preferably, $R^1$, $R^2$ and $R^4$ are hydrogen, methyl or ethyl.

In still other embodiments, $R^1$ and $R^2$ are alkanyl. Preferably, $R^1$ and $R^2$ are methyl or ethyl.

In still other embodiments, $R^1$ is alkanyl, substituted alkanyl, alkenyl, substituted alkenyl, aryl, substituted aryl, arylalkyl, substituted arylalkyl, cycloalkyl or substituted cycloalkyl. Preferably, $R^1$ and $R^2$ taken together are alkyleno, substituted alkyleno, heteroalkyleno or substituted heteroalkyleno. More preferably, $R^1$ and $R^2$ taken together are alkyleno or heteroalkyleno.

In still other embodiments, $R^1$ and $R^2$ taken together, $R^2$ and $R^3$ taken together and $R^2$ and $R^4$ taken together are alkyleno, substituted alkyleno, heteroalkyleno or substituted heteroalkyleno. Preferably, $R^1$ and $R^2$ taken together, $R^2$ and $R^3$ taken together and $R^2$ and $R^4$ taken together are alkyleno. Preferably, $R^1(R^2)(R^3)(R^4)N$ has the structure:

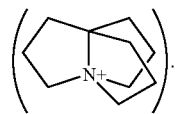

In still other embodiments, $R^3$ and $R^7$ taken together are alkyleno, substituted alkyleno, heteroalkyleno or substituted heteroalkyleno. Preferably, $R^3$ and $R^7$ taken together are alkyleno or heteroalkyleno.

In still other embodiments, $R^1$, $R^2$ and $R^4$ are hydrogen, alkanyl or substituted alkanyl and $R^3$ is alkyl, substituted alkyl, alkenyl, aryl, arylalkyl, cycloalkyl or $R^3$ and $R^7$ taken together are alkyleno, substituted alkyleno, heteroalkyleno or substituted heteroalkyleno. Preferably, $R^1$, $R^2$ and $R^4$ are methyl or ethyl and $R^3$ is alkyl, substituted alkyl, alkenyl, aryl, arylalkyl, cycloalkyl or $R^3$ and $R^7$ taken together are alkyleno or heteroalkyleno. Preferably, $R^1$, $R^2$ and $R^1$ are methyl or ethyl and $R^3$ is alkyl, substituted alkyl, alkenyl, aryl, arylalkyl or cycloalkyl.

In still other embodiments, $R^1(R^2)(R^3)(R^4)N$ is

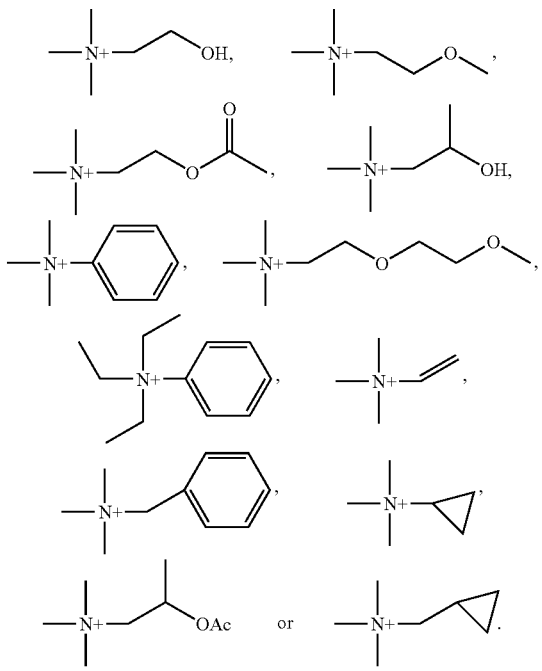

In still other embodiments, $R^1(R^2)(R^3)(R^4)N$ is

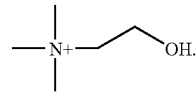

In still other embodiments, $R^1(R^2)(R^3)(R^4)N$ is

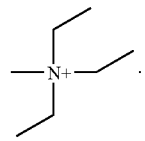

In still other embodiments, $R^1$, $R^2$ and $R^4$ are methyl or ethyl and $R^3$ and $R^7$ taken together are alkyleno or heteroalkyleno. Preferably, $R^1(R^2)(R^3)(R^4)N$ has the structure:

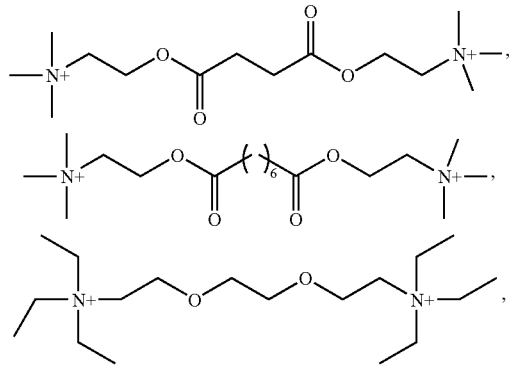

-continued

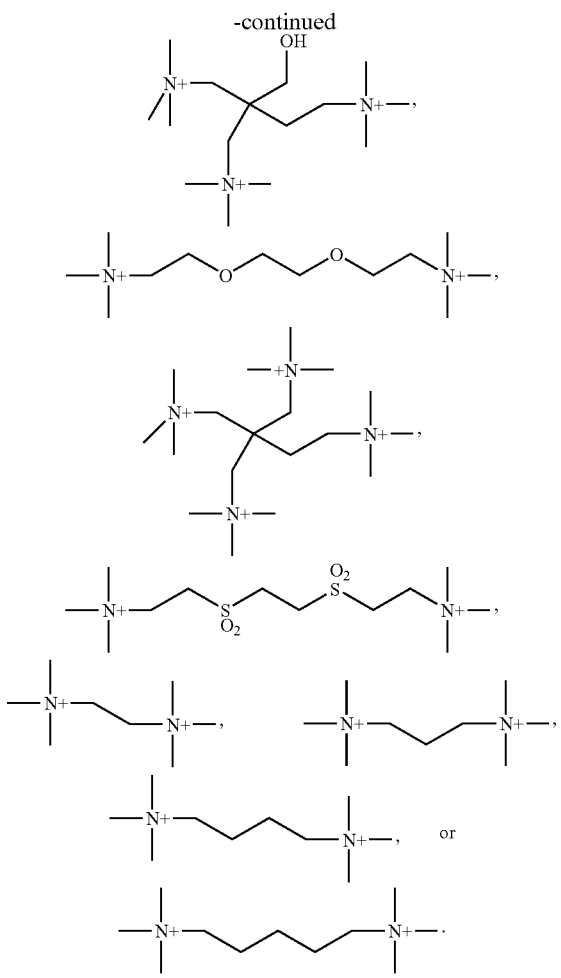

In still other embodiments, $R^1$, $R^2$ and $R^4$ are hydrogen and $R^3$ is substituted alkyl, cycloalkyl or substituted heteroaryl or $R^3$ and $R^7$ taken together are alkyleno. In still another embodiment, $R^1$ and $R^2$ are alkanyl and $R^3$ and $R^4$ are alkyl, substituted alkyl, aryl, arylalkyl or alkyleno. Preferably, $R^1$ and $R^2$ are methyl or ethyl and $R^3$ and $R^4$ are alkyl, substituted alkyl, aryl, arylalkyl or alkyleno.

In still other embodiments, $R^1(R^2)(R^3)(R^4)N$ are

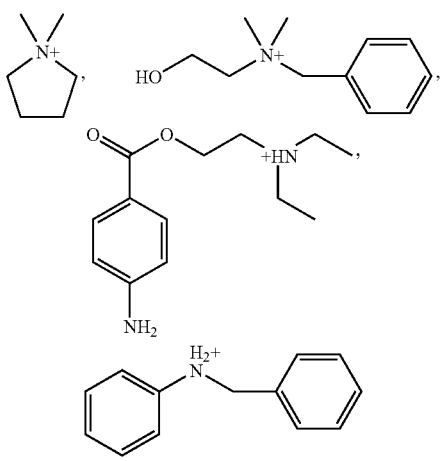

-continued

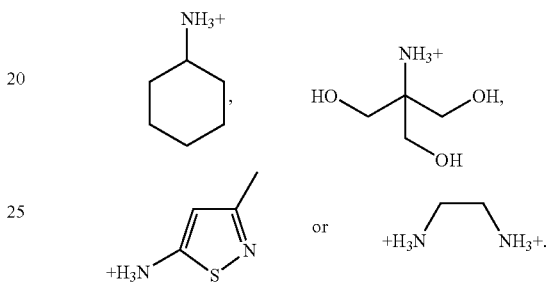

wherein $R^9$ is a mixture of straight chain alkanyl groups which have at least eight carbon atoms and not more than eighteen carbon atoms.

In still other embodiments, $R^1$, $R^2$ and $R^4$ are hydrogen and $R^3$ is substituted alkyl, substituted heteroaryl, cycloalkyl or alkyleno. Preferably, $R^1(R^2)(R^3)(R^4)N$ has the structure:

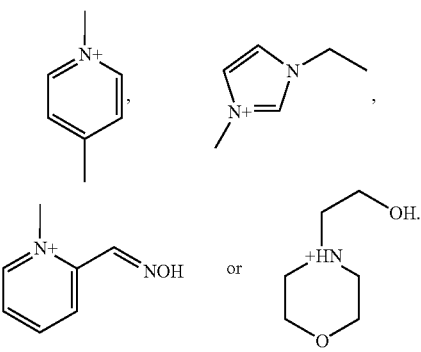

In still other embodiments, $R^1$ and $R^2$ taken together are alkyleno, substituted alkyleno, heteroalkyleno or substituted heteroalkyleno, $R^3$ is alkyl or substituted alkyl and $R^4$ is hydrogen or is absent. Preferably, $R^1(R^2)(R^3)N$ or $R^1(R^2)(R^3)(R^4)N$ has the structure:

5.3 Synthesis of Compounds

The compounds described herein may be obtained via conventional synthetic methods illustrated in Schemes 1 and 2. Starting materials useful for preparing compounds described herein and intermediates thereof are commercially available or can be prepared by well-known synthetic methods. Substituted ammonium salts (e.g., ammonium hydroxide and ammonium halides) may be either purchased from commercial sources or may be readily synthesized using well-known synthetic methods (Harrison et al., "Compendium of Synthetic Organic Methods", Vols. 1-8 (John Wiley and Sons, 1971-1996); "Beilstein Handbook of Organic Chemistry," Beilstein Institute of Organic Chemistry, Frankfurt, Germany; Feiser et al., "Reagents for Organic Synthesis," Volumes 1-17, Wiley Interscience; Trost et al., "Comprehensive Organic Synthesis," Pergamon Press, 1991; "Theilheimer's Synthetic Methods of Organic Chemistry," Volumes 1-45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesis of the compounds described herein and/or starting materials are either described in the art or will be readily apparent to the skilled artisan. Accordingly, the methods presented in Schemes 1 and 2 herein are illustrative rather than comprehensive.

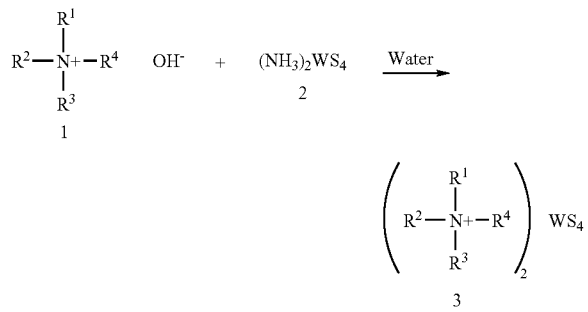

As shown above, in Scheme 1, addition of a quaternary ammonium hydroxide to thiotungstate in the presence of water leads to cation exchange (equilibrium to product is driven by removal of volatile ammonia) to provide the desired thiotungstate derivative.

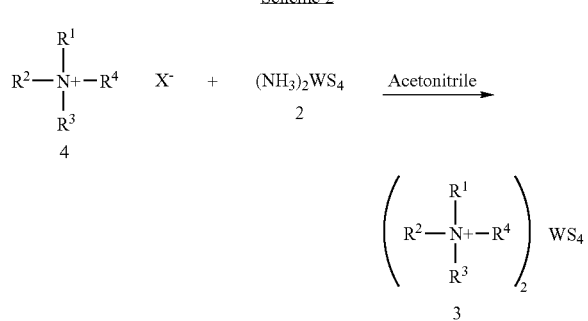

As shown above, in Scheme 2, addition of a quaternary ammonium halide to thiotungstate in the presence of acetonitrile leads to cation exchange (equilibrium to product is driven by formation of ammonium halide) to provide the desired thiotungstate derivative.

It should be noted that thiotungstate derivatives where the ammonium counterions are different may be prepared from compounds 3 by treating with one equivalent of a different ammonium counterion. Such a reaction would be expected to produce a statistical mixture of products.

Further, those of skill in the art will appreciate that conventional methods comprising treating tungstate with an ammonium salt and hydrogen sulfide may be used to synthesize many of the compounds described herein.

5.4 Assays

Those of skill in the art will appreciate that the in vitro and in vivo assays useful for measuring the activity of the compounds described herein are illustrative rather than comprehensive.

5.4.1 Assay for Endothelial Cell Migration

For endothelial cell migration, transwells are coated with type I collagen (50 μg/mL) by adding 200 μL of the collagen solution per transwell, then incubating overnight at 37° C. The transwells are assembled in a 24-well plate and a chemoattractant (e.g., FGF-2) is added to the bottom chamber in a total volume of 0.8 mL media. Endothelial cells such as human umbilical vein endothelial cells ("HUVEC"), which have been detached from monolayer culture using trypsin, are diluted to a final concentration of about $10^6$ cells/mL with serum-free media and 0.2 mL of this cell suspension is added to the upper chamber of each transwell. Inhibitors are added to both the upper and lower chambers, and the migration is allowed to proceed for 5 hrs in a humidified atmosphere at 37° C. The transwells are removed from the plate stained using DiffQuik®. Cells which did not migrate are removed from the upper chamber by scraping with a cotton swab and the membranes are detached, mounted on slides, and counted under a high-power field (400x) to determine the number of cells migrated.

5.4.2 Biological Assay of Anti-Invasive Activity

Compounds and/or compositions are tested for their anti-invasive capacity. The ability of cells such as endothelial cells or tumor cells (e.g., PC-3 human prostatic carcinoma) cells to invade through a reconstituted basement membrane (Matrigel®) in an assay known as a Matrigel® invasion assay (Kleinman et al., Biochemistry 1986, 25: 312-318; Parish et al., Int. J. Cancer 1992, 52:378-383). Matrigel® is a reconstituted basement membrane containing type IV collagen, laminin, heparan sulfate proteoglycans such as perlecan, which bind to and localize bFGF, vitronectin as well as transforming growth factor-β (TGFβ, urokinase-type plasminogen activator (uPA), tissue plasminogen activator (tPA), and the serpin known as plasminogen activator inhibitor type 1 (PAI-1)) (Chambers et al., Canc. Res. 1995, 55:1578-1585). Results obtained in this assay for compounds which target extracellular receptors or enzymes are typically predictive of the efficacy of these compounds in vivo (Rabbani et al., 1995, Int. J Cancer 63: 840-845).

Such assays employ transwell tissue culture inserts. Invasive cells are defined as cells which are able to traverse through the Matrigel® and upper aspect of a polycarbonate membrane and adhere to the bottom of the membrane. Transwells (Costar) containing polycarbonate membranes (8.0 μm pore size) are coated with Matrigel® (Collaborative Research), which has been diluted in sterile PBS to a final concentration of 75 μg/mL (60 μL of diluted Matrigel® per insert), and placed in the wells of a 24-well plate. The membranes are dried overnight in a biological safety cabinet, then rehydrated by adding 100 μL of DMEM containing antibiotics for 1 hour on a shaker table. The DMEM is removed from each insert by aspiration and 0.8 mL of DMEM/10% FBS/antibiotics is added to each well of the 24-well plate such that it surrounds the outside of the transwell ("lower chamber").

Fresh DMEM/antibiotics (100 μL), human Glu-plasminogen (5 μg/mL), and any compounds to be tested are added to the top, inside of the transwell ("upper chamber"). The cells which are to be tested are trypsinized and resuspended in DMEM/antibiotics, then added to the top chamber of the transwell at a final concentration of 800,000 cells/mL. The final volume of the upper chamber is adjusted to 200 μL. The assembled plate is then incubated in a humid 5% $CO_2$ atmosphere for 72 hours. After incubation, the cells are fixed and stained using DiffQuik® (Giemsa stain) and the upper chamber is then scraped using a cotton swab to remove the Matrigel® and any cells which did not invade through the membrane. The membranes are detached from the transwell using an X-acto® blade, mounted on slides using Permount® and cover-slips, then counted under a high-powered (400×) field. An average of the cells invaded is determined from 5-10 fields counted and plotted as a function of inhibitor concentration.

5.4.3 Tube-Formation Assays of Anti-Angiogenic Activity

Compounds may be tested for anti-angiogenic activity in one of two different assay systems in vitro.

Endothelial cells, for example, human umbilical vein endothelial cells ("HUVEC") or human microvascular endothelial cells ("HMVEC") which can be prepared or obtained commercially, are mixed at a concentration of $2 \times 10^5$ cells/mL with fibrinogen (5 mg/mL in phosphate buffered saline ("PBS") in a 1:1 (v/v) ratio. Thrombin is added (5 units/mL final concentration) and the mixture is immediately transferred to a 24-well plate (0.5 mL per well). The fibrin gel is allowed to form and then VEGF and bFGF are added to the wells (each at 5 ng/mL final concentration) along with the test compound. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g., 0 or 1 branch). This assay is recognized in the art to be predictive of angiogenic (or anti-angiogenic) efficacy in vivo (Min et al., *Cancer Res.* 1996, 56: 2428-2433).

In an alternate assay, endothelial cell tube formation is observed when endothelial cells are cultured on Matrigel® (Schnaper et al., *J. Cell. Physiol.* 1995, 165:107-118). Endothelial cells ($1 \times 10^4$ cells/well) are transferred onto Matrigel®-coated 24-well plates and tube formation is quantitated after 48 hours. Inhibitors are tested by addition at either the same time as the endothelial cells or at various time points thereafter. Tube formation can also be stimulated by adding angiogenic growth factors such as bFGF or VEGF, differentiation stimulating agents (e.g., PMA) or combinations thereof.

This assay models angiogenesis by presenting a particular type of basement membrane to the endothelial cells, namely the layer of matrix, which migrating and differentiating endothelial cells might be expected to first encounter. In addition, the matrix components found in Matrigel® (and in basement membranes in situ) or proteolytic products thereof may also be stimulatory for endothelial cell tube formation which makes this model complementary to the fibrin gel angiogenesis model previously described (Blood et al., *Biochim. Biophys. Acta* 1990, 1032:89-118; Odedra et al., *Pharmac. Ther.* 1991, 49:111-124). The compounds inhibit endothelial cell tube formation in both assays, which suggests that the compounds will also have anti-angiogenic activity.

5.4.4 Assays for Inhibition of Proliferation

The ability of the compounds to inhibit the proliferation of endothelial cells may be determined in a 96-well format. Type I collagen (gelatin) is used to coat the wells of the plate (0.1-1 mg/mL in PBS, 0.1 mL per well for 30 minutes at room temperature). After washing the plate (3× w/PBS), 3-6,000 cells are plated per well and allowed to attach for 4 hours (37° C./5% $CO_2$) in Endothelial Growth Medium (EGM; Clonetics) or M199 media containing 0.1-2% FBS. The media and any unattached cells are removed at the end of 4 hours and fresh media containing bFGF (1-10 ng/mL) or VEGF (1-10 ng/mL) is added to each well. Compounds to be tested are added last and the plate is allowed to incubate (37° C./5% $CO_2$) for 24-48 hrs. MTS (Promega) is added to each well and allowed to incubate from 1-4 hrs. The absorbance at 490 nm, which is proportional to the cell number, is then measured to determine the differences in proliferation between control wells and those containing test compounds. A similar assay system can be set up with cultured adherent tumor cells. However, collagen may be omitted in this format. Tumor cells (e.g., 3,000-10,000/well) are plated and allowed to attach overnight. Serum free medium is then added to the wells and the cells are synchronized for 24 hrs. Medium containing 10% FBS is then added to each well to stimulate proliferation. Compounds to be tested are included in some of the wells. After 24 hrs, MTS is added to the plate and the assay developed and read as described above. A similar methodology may also be employed to evaluate the effects of the compounds of the invention on the proliferation of other cell types including tumor cells except that VEGF and bFGF would not be used to stimulate growth of the cells. If there is evidence of anti-proliferative activity, induction of apoptosis may be measured using TumorTACS (Genzyme).

5.4.5 Assays of Cytotoxicity

The cytotoxic effects of compounds described herein may be determined for various cell types including tumor cells, endothelial cells, fibroblasts and macrophages.

A typical assay involves plating cells at a density of 5-10, 000 cells per well in a 96-well plate. Compounds are then added at a variety of concentrations and allowed to incubate with the cells for 24 hours. The cells are washed 3× with media. For cytotoxicity assays (measuring cell lysis), a Promega 96-well cytotoxicity kit is used.

5.4.6 Corneal Angiogenesis Model

The protocol used is essentially identical to that described by Volpert et al., *J. Clin. Invest.* 1996, 98:671-679. Briefly, female Fischer rats (120-140 gms) are anesthetized and pellets (5 μl) comprised of Hydron®, bFGF (150 nM) and the compounds to be tested are implanted into tiny incisions made in the cornea 1.0-1.5 mm from the limbus. Neovascularization is assessed at 5 and 7 days after implantation. On day 7, animals are anesthetized and infused with a dye such as colloidal carbon to stain the vessels. The animals are then euthanized, the corneas fixed with formalin, and the corneas flattened and photographed to assess the degree of neovascularization. Neovessels may be quantitated by imaging the total vessel area or length or simply by counting vessels.

5.4.7 Matrizel® Plug Assay

This assay is performed essentially as described by Passaniti et al., *Lab Invest.* 1992, 67:519-528. Ice-cold Matrigel® (e.g., 500 μL) (Collaborative Biomedical Products, Inc., Bedford, Mass.) is mixed with heparin (e.g., 50 μg/ml), FGF-2 (e.g., 400 ng/ml) and the compound to be tested. In some assays, bFGF may be substituted with tumor cells as the angiogenic stimulus. The Matrigel® mixture is injected subcutaneously into 4-8 week-old athymic nude mice at sites near the abdominal midline, preferably 3 injections per mouse. The injected Matrigel®b forms a palpable solid gel. Injection sites are chosen such that each animal receives a positive control plug (such as FGF-2+heparin), a negative control plug (e.g., buffer+heparin) and a plug that includes the compound being tested for its effect on angiogenesis (e.g., FGF-2+heparin+compound). All treatments are preferably run in triplicate. Animals are sacrificed by cervical dislocation at about 7 days post injection or another time that may be optimal for observing angiogenesis. The mouse skin is detached along the abdominal midline, and the Matrigel® plugs are recovered and scanned immediately at high resolution. Plugs are then dispersed in water and incubated at 37° C. overnight. Hemoglobin (Hb) levels are determined using Drabkin's solution (e.g., obtained from Sigma) according to the manufacturers' instructions. The amount of Hb in the plug is an indirect measure of angiogenesis as it reflects the amount of blood in the sample. In addition, or alternatively, animals may be injected prior to sacrifice with a 0.1 ml buffer (preferably PBS) containing a high molecular weight dextran to which is conjugated a fluorophore. The amount of fluorescence in the dispersed plug which is determined fluorimetrically serves as a measure of angiogenesis in the plug. Staining with mAb anti-CD31 (CD31 is platelet-endothelial cell adhesion molecule or "PECAM") may also be used to confirm neovessel formation and microvessel density in the plugs.

5.4.8 Chick Chorioallantoic Membrane (CAM) Angiogenesis Assay

This assay is performed essentially as described by Nguyen et al., *Microvascular Res.* 1994, 47:31-40. A mesh containing either angiogenic factors (bFGF) or tumor cells plus inhibitors is placed onto the CAM of an 8-day old chick embryo and the CAM observed for 3-9 days after implantation of the sample. Angiogenesis is quantitated by determining the percentage of squares in the mesh which contain blood vessels.

5.4.9 In Vivo Assessment Angioienesis Inhibition and Anti-Tumor Effects Using the Matrigel® Plug Assay with Tumor Cells In this assay, tumor cells, for example, 1-5×10$^6$ cells of the 3LL Lewis lung carcinoma or the rat prostate cell line Mat-LyLu, are mixed with Matrigel® and then injected into the flank of a mouse following the protocol described in section 4.4.7 above. A mass of tumor cells and a powerful angiogenic response can be observed in the plugs after about 5 to 7 days. The anti-tumor and anti-angiogenic action of a compound in an actual tumor environment can be evaluated by including it in the plug. Measurement is then made of tumor weight, Hb levels or fluorescence levels (of a dextran-fluorophore conjugate injected prior to sacrifice). To measure Hb or fluorescence, the plugs are first homogenized with a tissue homogenizer.

5.4.10 Xenograft Model of Subcutaneous Tumor Growth

Nude mice are inoculated with MDA-MB-23.1 cells (human breast carcinoma) and Matrigel® (1×10$^6$ cells in 0.2 mL) subcutaneously in the right flank of the animals. The tumors are staged to 200 mm$^3$ and then treatment with a test compound is initiated. Tumor volumes are obtained every other day and the animals are sacrificed after 2 weeks of treatment. The tumors are excised, weighed and paraffin embedded. Histological sections of the tumors are analyzed by H and E, anti-CD31, Ki-67, TUNEL, and CD68 staining.

Other human tumor cell lines including but not limited to PC-3, CWR$^{22}$R, SK-OV-3, A2780, A549, HCT116, HT29 may also be used to test the anti-tumor activity of the compounds described herein in a similar manner.

5.4.11 Xenograft Model of Metastasis

The compounds may also be tested for inhibition of late metastasis using an experimental metastasis model (Crowley et al., *Proc. Natl. Acad. Sci. USA* 1993, 90 5021-5025). Late metastasis involves the steps of attachment and extravasation of tumor cells, local invasion, seeding, proliferation and angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This approach permits utilization of either of these markers (fluorescence detection of GFP or histochemical calorimetric detection of enzymatic activity) to follow the fate of these cells. Cells are injected, preferably, i.v., and metastases identified after about 14 days, particularly in the lungs but also in regional lymph nodes, femurs and brain. This mimics the organ tropism of naturally occurring metastases in human prostate cancer. For example, GFP-expressing PC-3 cells (1×10$^6$ cells per mouse) are injected i.v. into the tail veins of nude (nu/nu) mice. Animals are treated with a test composition at 100 μg/animal/day given q.d. IP. Single metastatic cells and foci are visualized and quantitated by fluorescence microscopy or light microscopic histochemistry or by grinding the tissue and quantitative colorimetric assay of the detectable label.

5.4.12 Inhibition of Spontaneous Metastasis In Vivo by HPRG and Functional Derivatives The rat syngeneic breast cancer system (Xing et al., *Int. J. Cancer* 1996, 67:423-429) employs Mat BIII rat breast cancer cells. Tumor cells, for example about 10$^6$ suspended in 0.1 mL PBS, are inoculated into the mammary fat pads of female Fisher rats. At the time of inoculation, a 14-day Alza osmotic mini-pump is implanted intraperitoneally to dispense the test compound. The compound is dissolved in PBS (e.g., 200 mM stock), sterile filtered and placed in the minipump to achieve a release rate of about 4 mg/kg/day. Control animals receive vehicle (PBS) alone or a vehicle control peptide in the minipump. Animals are sacrificed at about day 14.

Other models of experimental metastasis may also be used to evaluate the compounds described herein. These models would utilize the human tumor cell lines described, supra, injected through the tail vein of a nude mouse. Typically, these mice are sacrificed 28 days after tumor cell inoculation and their lungs evaluated for the presence of metastases.

5.4.13 3LL Lewis Lung Carcinoma: Primary Tumor Growth

This tumor line arose spontaneously in 1951 as carcinoma of the lung in a C57BL/6 mouse (*Cancer Res.* 1955, 15:39. See, also Malave et al., *J. Nat'l. Canc. Inst.* 1979, 62:83-88).

It is propagated by passage in C57BL/6 mice by subcutaneous inoculation and is tested in semiallogeneic C57BL/6× DBA/2 F$_1$ mice or in allogeneic C3H mice. Typically six animals per group for subcutaneously implant, or ten for intramuscular implant are used. Tumor may be implanted by subcutaneous inoculation as a 2-4 mm fragment or intramuscularly implanted or subcutaneous implanted as an inoculum of suspended cells of about 0.5-2×10$^6$-cells. Treatment begins 24 hours after implant or is delayed until a tumor of specified size (usually approximately 400 mg) can be palpated. The test compound is administered i.p. daily for 11 days Animals are followed by weighing, palpation, and measurement of tumor size. Typical tumor weight in untreated control recipients on day 12 after intramuscular inoculation is 500-2500 mg. Typical median survival time is 18-28 days. A positive control compound, for example, cyclophosphamide at 20 mg/kg/injection per day on days 1-11 is used. Results computed include mean animal weight, tumor size, tumor weight and survival time. For confirmed therapeutic activity, the test composition should be tested in two multi-dose assays.

5.4.14 3LL Lewis Lung Carcinoma: Primary Growth and Spontaneous Metastasis Model This model has been utilized by a number of investigators (See, for example, Gorelik et al., 1980, *J. Nat'l. Canc. Inst.* 65:1257-1264; Gorelik et al., *Rec. Results Canc. Res.* 1980, 75:20-28; Isakov et al., *Invasion Metas.* 1982, 2:12-32; Talmadge et al., *J. Nat'l. Canc. Inst.* 1982, 69:975-980; Hilgard et al., *Br. J. Cancer* 1977, 35:78-86). Test mice are male C57BL/6 mice, 2-3 months old. Following subcutaneous, intramuscular or intra-footpad implantation, this tumor produces metastases, preferentially in the lungs. With some lines of the tumor, the primary tumor exerts anti-metastatic effects and must first be excised before study of the metastatic phase (see also, O'Reilly et al., U.S. Pat. No. 5,639,725).

Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95-99% (by trypan blue dye exclusion). Viable tumor cells (3×10$^4$-5×10$^6$) suspended in 0.05 ml PBS are injected subcutaneously, either in the dorsal region or into one hind foot pad of C57BL/6 mice. Visible tumors appear after 3-4 days after dorsal sc injection of 10$^6$ cells. The day of tumor appearance and the diameters of established tumors are measured by caliper every two days.

The treatment is given as one or two doses of compound, per week. In another embodiment, the compound is delivered by osmotic minipump.

In experiments involving tumor excision of dorsal tumors, when tumors reach about 1500 mm$^3$ in size, mice are randomized into two groups: (1) primary tumor is completely excised; or (2) sham surgery is performed and the tumor is left intact. Although tumors from 500-3000 mm$^3$ inhibit growth of metastases, 1500 mm$^3$ is the largest size primary tumor that can be safely resected with high survival and without local regrowth. After 21 days, all mice are sacrificed and autopsied.

Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakir et al., *J. Lab. Clin. Med.* 1977, 89:217-228). Ten days following tumor amputation, 25 µg of fluorodeoxyuridine is inoculated into the peritoneums of tumor-bearing (and, if used, tumor-resected mice). After 30 min, mice are given 1 µCi of $^{125}$IdUrd (iododeoxyuridine). One day later, lungs and spleens are removed and weighed and a degree of $^{125}$IdUrd incorporation is measured using a gamma counter.

In mice with footpad tumors, when tumors reach about 8-10 mm in diameter, mice are randomized into two groups: (1) legs with tumors are amputated after ligation above the knee joints; or (2) mice are left intact as nonamputated tumor-bearing controls. (Amputation of a tumor-free leg in a tumor-bearing mouse has no known effect on subsequent metastasis, ruling out possible effects of anesthesia, stress or surgery). Mice are killed 10-14 days after amputation. Metastases are evaluated as described above.

5.5 Therapeutic Uses

A compound of structural formula (I) and/or a pharmaceutical composition thereof is administered to a patient, preferably a human, suffering from a disease characterized by aberrant vascularization. Aberrant vascularization includes abnormal neovascularization such as the formation of new blood vessels, larger blood vessels, more branched blood vessels and any other mechanism, which leads to an increased blood carrying capacity to a diseased tissue or site. The compounds and pharmaceutical compositions thereof may be used to treat and/or prevent aberrant vascularization.

Preferably, diseases characterized by aberrant vascularization include, but are not limited to, cancer (e.g., any vascularized tumor, preferably, a solid tumor, including but not limited to, carcinomas of the lung, breast, ovary, stomach, pancreas, larynx, esophagus, testes, liver, parotid, bilary tract, colon, rectum, cervix, uterus, endometrium, kidney, bladder, prostrate, thyroid, squamous cell carcinomas, adenocarcinomas, small cell carcinomas, melanomas, gliomas, neuroblastomas, sarcomas (e.g., angiosarcomas, chondrosarcomas)), arthritis, diabetes, arteriosclerosis, arteriovenous, malformations, corneal graft neovascularization, delayed wound healing, diabetic retinopathy, age related macular degeneration, granulations, burns, hemophilic joints, rheumatoid arthritis, hypertrophic scars, neovascular glaucoma, nonunion fractures, Osier Weber Syndrome, psoriasis, granuloma, retrolental fibroplasia, pterygium, scleroderma, trachoma, vascular adhesions, ocular neovascularization, parasitic diseases, hypertrophy following surgery, inhibition of hair growth, macular degeneration (including both wet and dry type), rheumatoid arthritis and osteoarthritis. Diseases characterized by aberrant vascularization which are preferably treated and/or prevented by administration of a compound of structural formula (I) and/or a pharmaceutical composition thereof include cancer, macular degeneration and rheumatoid arthritis.

Further, a compound of structural formula (I) and/or a pharmaceutical composition thereof may be administered to a patient, preferably a human, suffering from a disease associated with copper metabolism disorders (e.g., Wilson's disease) to treat and/or prevent such a disease.

Still further, a compound of structural formula (I) and/or a pharmaceutical composition thereof may be administered to a patient, preferably a human, to treat and/or prevent obesity. The compounds of structural formula (I) may be also used to reduce levels of inflammatory cytokines (e.g., TNF-α, TNF-β, IL-8, etc.) and plasminogen activator inhibitor, which may be associated with angiogenesis and obesity (Loskutoff et al., *Ann. N. Y Acad. Sci.*, 2000, 902:272-281; Pan et al., *Cancer Res.*, 2002, 62:4854-4859; Hanada et al., *Cytokine Growth Factor Rev.* 2002, 13:413-421; Chen et al., *Science* 2002, 296:1634-5; Miyake et al., *J. Neuropathol. Exp. Neurol.* 59:18-28; Koch et al., *Science* 1992, 258:1798-801; Osawa et al., *Infect. Immun.* 2002, 70:6294-6301; Bajou et al., *Nat. Med.* 1998, 4:923-8).

Still further, a compound of structural formula (I) and/or a pharmaceutical composition thereof may be administered to a patient, preferably a human, suffering from a neurodegenerative disorder, to treat and/or prevent the neurodegenerative disorder. Elevated levels of copper have been reported in the art to mediate the pathobiology of various neurodegenerative disorders including Alzheimer's disease, amyotrophic lateral sclerosis (ALS) and prion disease (Llanos et al., *DNA Cell Biol.* 2002, 21: 259-270; Carri et al., *Funct. Neurol* 2001, 16:181-188; Perry et al., *CNS Drugs* 2002, 16:339-352; Kowalik-Jankowska et al., *Environ Health Perspect,* 2002, 5: 869-870; Maynard et al., *J. Biol. Chem.* 2002, 277, 44670-44676; Gnjec et al., *Front Biosci.* 2002, 16-23; Strausak et al., *Brain Res. Bull.* 2001, 55: 175-185; Brown, *Brain Res. Bull.* 2001, 55:165-173; Brown, *Biochem. Soc. Trans* 2002, 30:742-745).

Still further, in accordance with the invention, a compound of structural formula (I) and/or a pharmaceutical composition thereof may be administered to a patient, preferably a human, to treat diseases characterized by dysregulated activity of the NF-κB or dysregulated inflammation of inflammatory response.

Further, in certain embodiments, a compounds and and/or pharmaceutical compositions thereof are administered to a patient, preferably, a human, as a preventative measure against various diseases or disorders characterized by aberrant vascularization, copper metabolism disorders, neurodegenerative disorders, obesity or NF-κB dysregulation. Accordingly, compounds of structural Formula (I) and/or pharmaceutical compositions thereof may be used for the prevention of one disease or disorder and concurrently treating another (e.g., preventing Wilson's disease or Alzheimer's while treating cancer).

5.6 Therapeutic/Prophylactic Administration

The compounds of structural Formula (I) and/or pharmaceutical compositions thereof may be advantageously used in human medicine. As previously described in Section 4.5, supra, compounds of structural Formula (I) and/or pharmaceutical compositions thereof are useful for the treatment and/or prevention of various diseases or disorders characterized by aberrant vascularization, copper metabolism disorders, neurodegenerative disorders, obesity or NF-κB dysregulation.

When used to treat and/or prevent the above disease or disorders, compounds of structural Formula (I) and/or pharmaceutical compositions may be administered or applied singly, or in combination with other agents. The compounds of structural Formula (I) and/or pharmaceutical compositions thereof may also be administered or applied singly, in combination with other pharmaceutically active agents (e.g., other anti-cancer agents, other anti-angiogenic agents, other chelators such as zinc, penicillamine, etc. and other anti-obesity agents, including other compounds of structural Formula (I) and/or pharmaceutical compositions thereof.

Methods of treatment and prophylaxis by administration to a patient of a therapeutically effective amount of a compound of structural Formula (I) and/or pharmaceutical composition thereof are provided herein. The patient may be an animal, more preferably, a mammal and most preferably, a human.

The present compounds of structural Formula (I) and/or pharmaceutical compositions thereof, are preferably administered orally. The compounds of structural Formula (I) and/or pharmaceutical compositions thereof may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound of structural Formula (I) and/or pharmaceutical composition thereof. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the compounds of structural Formula (I) and/or pharmaceutical compositions thereof into the bloodstream.

In specific embodiments, it may be desirable to administer one or more compounds of structural Formula (I) and/or pharmaceutical composition thereof locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of aberrant vascularization (e.g., cancer or arthritis).

In certain embodiments, it may be desirable to introduce one or more compounds of structural Formula (I) and/or pharmaceutical compositions thereof into the central nervous system by any suitable route, including intraventricular, intrathecal and epidural injection. Intraventricular injection may be facilitated by an intraventricular catheter, for example, attached to a reservoir, such as an Ommaya reservoir.

A compound of structural Formula (I) and/or pharmaceutical composition thereof may also be administered directly to the lung by inhalation. For administration by inhalation, a compound of structural Formula (I) and/or pharmaceutical composition thereof may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of structural Formula (I) and/or pharmaceutical compositions thereof directly to the lung.

Alternatively, a Dry Powder Inhaler ("DPI") device may be used to administer a compound of structural Formula (I) and/or pharmaceutical thereof to the lung. DPI devices typically use a mechanism such as a burst of gas to create a cloud of dry powder inside a container, which may then be inhaled by the patient. DPI devices are also well known in the art. A popular variation is the multiple dose DPI ("MDDPI") system, which allows for the delivery of more than one therapeutic dose. For example, capsules and cartridges of gelatin for use in an inhaler or insufflator may be formulated containing a powder mix of a compound of structural Formula (I) and a suitable powder base such as lactose or starch for these systems.

Another type of device that may be used to deliver a compound of structural Formula (I) and/or pharmaceutical composition thereof to the lung is a liquid spray device supplied, for example, by Aradigm Corporation, Hayward, Calif. Liquid spray systems use extremely small nozzle holes to aerosolize liquid drug formulations that may then be directly inhaled into the lung.

In one embodiment, a nebulizer is used to deliver a compound of structural Formula (I) and/or pharmaceutical composition thereof to the lung. Nebulizers create aerosols from liquid drug formulations by using, for example, ultrasonic energy to form fine particles that may be readily inhaled (see e.g., Verschoyle et al., *British J. Cancer,* 1999, 80, Suppl. 2, 96). Examples of nebulizers include devices supplied by Sheffield Pharmaceuticals, Inc (See, Armer et al., U.S. Pat. No. 5,954,047; van der Linden et al., U.S. Pat. No. 5,950,619; van der Linden et al., U.S. Pat. No. 5,970,974), and Batelle Pulmonary Therapeutics, Columbus, Ohio.

In another embodiment, an electrohydrodynamic ("EHD") aerosol device is used to deliver a compound of structural Formula (I) and/or pharmaceutical composition thereof to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering a compound of structural Formula (I) and/or pharmaceutical composition thereof to the lung with an EHD aerosol device and such optimization is routinely performed by one of skill in the art. EHD aerosol devices may more efficiently deliver compounds to the lung than other pulmonary delivery technologies.

In some embodiments, the compounds of structural Formula (I) and/or pharmaceutical compositions thereof can be delivered in a vesicle, in particular a liposome (See, Langer, 1990, *Science* 249:1527-1533; Treat et al., in "Liposomes in the Therapy of Infectious Disease and Cancer," Lopez-Berestein and Fidler (eds.), Liss, New York, pp. 353-365 (1989); see generally "Liposomes in the Therapy of Infectious Disease and Cancer," Lopez-Berestein and Fidler (eds.), Liss, N.Y., pp. 353-365 (1989)).

In other embodiments, the compounds of structural Formula (I) and/or pharmaceutical compositions thereof can be delivered via sustained release systems, preferably oral sustained release systems. In one embodiment, a pump may be used (See, Langer, supra, Sefton, 1987, *CRC Crit. Ref Biomed Eng.* 14:201; Saudek et al., 1989, *N. Engl. J Med.* 321:574).

In yet other embodiments, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macromol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In still other embodiments, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, *Int. J. Pharm. Tech. & Prod. Mfr.,* 1984, 5(3) 1-9). Factors affecting drug release are well known to the skilled artisan and have been described in the art (Bamba et al., *Int. J. Pharm.,* 1979, 2, 307).

In still other embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still other embodiments, osmotic delivery systems are used for oral sustained release administration (Verma et al., *Drug Dev. Ind. Pharm.,* 2000, 26:695-708). In yet other embodiments, OROS™ osmotic devices are used for oral sustained release delivery devices (Theeuwes et al., U.S. Pat. No. 3,845,770; Theeuwes et al., U.S. Pat. No. 3,916,899).

In still other embodiments, a controlled-release system can be placed in proximity of the target of the compounds and/or pharmaceutical composition of the invention, thus requiring only a fraction of the systemic dose (See, e.g., Goodson, in "Medical Applications of Controlled Release," supra, vol. 2, pp. 115-138 (1984). Other controlled-release systems discussed in Langer, 1990, *Science* 249:1527-1533 may also be used.

5.7 Pharmaceutical Compositions

The present pharmaceutical compositions contain a therapeutically effective amount of one or more compounds of structural Formula (I), preferably in purified form, together with a suitable amount of a pharmaceutically acceptable vehicle, so as to provide the form for proper administration to a patient. When administered to a patient, the compounds of structural Formula (I) and pharmaceutically acceptable vehicles are preferably sterile. Water is a preferred vehicle when the compound of structural Formula (I) is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of structural Formula (I) may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of structural Formula (I) into preparations which can be used pharmaceutically. Proper formulation is dependent upon the route of administration chosen.

The present pharmaceutical compositions can take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698, 155). Other examples of suitable pharmaceutical vehicles have been described in the art (see Remington: The Science and Practice of Pharmacy, Philadelphia College of Pharmacy and Science, 20$^{th}$ Edition, 2000).

For topical administration a compound of structural Formula (I) may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In some embodiments, the compounds of structural Formula (I) are formulated in accordance with routine procedures as a pharmaceutical composition adapted for intravenous administration to human beings. Typically, compounds of structural Formula (I) for intravenous administration are solutions in sterile isotonic aqueous buffer. For injection, a compound of structural Formula (I) may be formulated in aqueous solutions, preferably in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of structural Formula (I) is administered by infusion, it can be dispensed, for example, with an infusion bottle containing sterile pharmaceutical grade water or saline. When the compound of structural Formula (I) is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation. Moreover, where in tablet or pill form, the pharmaceutical compositions may be coated to delay disintegration and absorption in the gastrointestinal tract, thereby providing a sustained action over an extended period of time. Selectively permeable membranes surrounding an osmotically active driving compound are also suitable for orally administered compounds of structural Formula (I). In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcamitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of structural Formula (I) with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound of structural Formula (I) may also be formulated in rectal or vaginal pharmaceutical compositions such as suppositories or retention enemas, e.g., containing conventional suppository bases such as cocoa butter or other glycerides.

In addition to the formulations described previously, a compound of structural Formula (I) may also be formulated as a depot preparation. Such long acting formulations may be administered by implantation (for example subcutaneously or intramuscularly) or by intramuscular injection. Thus, for example, a compound of structural Formula (I) may be formulated with suitable polymeric or hydrophobic materials (for example, as an emulsion in an acceptable oil) or ion exchange resins, or as sparingly soluble derivatives, for example, as a sparingly soluble salt.

When a compound of structural Formula (I) is acidic, it may be included in any of the above-described formulations as the free acid, a pharmaceutically acceptable salt, a solvate or hydrate. Pharmaceutically acceptable salts substantially retain the activity of the free acid, may be prepared by reaction with bases and tend to be more soluble in aqueous and other protic solvents than the corresponding free acid form.

5.8 Therapeutic Doses

A compound of structural Formula (I), and/or pharmaceutical composition thereof, will generally be used in an amount effective to achieve the intended purpose. For use to treat or prevent diseases or disorders characterized by aberrant vascularization, copper metabolism disorders, neurodegenerative disorders and obesity the compounds of structural Formula (I) and/or pharmaceutical compositions thereof, are administered or applied in a therapeutically effective amount.

The amount of a compound of structural Formula (I) that will be effective in the treatment of a particular disorder or condition disclosed herein will depend on the nature of the disorder or condition and can be determined by standard clinical techniques known in the art, as previously described. In addition, in vitro or in vivo assays may optionally be employed to help identify optimal dosage ranges. The amount of a compound of structural Formula (I) administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In one embodiment, the compounds of structural Formula (I) are delivered by oral sustained release administration. Preferably, in this embodiment, the compounds of structural Formula (D) are administered twice per day (more preferably, once per day). Dosing may be repeated intermittently, may be provided alone or in combination with other drugs and may continue as long as required for effective treatment of the disease state or disorder.

Suitable dosage ranges for oral administration depend on potency, but are generally between about 0.001 mg to about 200 mg of a compound of structural Formula (I) per kilogram body weight. Dosage ranges may be readily determined by methods known to the artisan of ordinary skill the art.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of structural Formula (I) per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

The compounds of structural Formula (I) are preferably assayed in vitro and in vivo, for the desired therapeutic or prophylactic activity, prior to use in humans. For example, in vitro assays can be used to determine whether administration of a specific compound of structural Formula (I) or a combination of compounds of structural Formula (I) is preferred for treating or preventing diseases or disorders characterized by aberrant vascularization, copper metabolism disorders, neurodegenerative disorders and obesity. The compounds of structural Formula (I) may also be demonstrated to be effective and safe using animal model systems.

Preferably, a therapeutically effective dose of a compound of structural Formula (I) described herein will provide therapeutic benefit without causing substantial toxicity. Toxicity of compounds of structural Formula (I) may be determined using standard pharmaceutical procedures and may be readily ascertained by the skilled artisan. The dose ratio between toxic and therapeutic effect is the therapeutic index. A compound of structural Formula (I) will preferably exhibit particularly high therapeutic indices in treating disease and disorders. The dosage of a compound of structural Formula (I) described herein will preferably be within a range of circulating concentrations that include an effective dose with little or no toxicity.

5.9 Combination Therapy

In certain embodiments of the present invention, the compounds of structural Formula (I) and/or pharmaceutical compositions thereof can be used in combination therapy with at least one other therapeutic agent or with radiation therapy. The compound of structural Formula (I) and/or pharmaceutical composition thereof and the other therapeutic agent can act additively or, more preferably, synergistically. In some embodiments, a compound of structural Formula (I) and/or pharmaceutical composition thereof is administered concurrently with the administration of another therapeutic agent, which may be part of the same pharmaceutical composition as the compound of structural Formula (I) or a different pharmaceutical composition. In other embodiments, a pharmaceutical composition of structural Formula (I) is administered prior or subsequent to administration of another therapeutic agent.

In some embodiments, the compounds of structural Formula (I) and/or pharmaceutical compositions thereof can be used in combination therapy with other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, triazines) antimetabolites (e.g., folic acid analogs, pyrimidine analogs (e.g., fluorouracil, floxuridine, cytosine arabinoside, etc.), purine analogs (e.g., mercaptopurine, thiogunaine, pentostatin, etc.), natural products (e.g., vinblastine, vincristine, etoposide, tertiposide, dactinomycin, daunorubicin, doxurubicin, bleomycin, mithrmycin, mitomycin C, L-asparaginase, interferon alpha), platinum coordination complexes (e.g., cis-platinum, carboplatin, etc.), mitoxantrone, hydroxyurea, procarbazine, hormones and antagonists (e.g., prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, etc.), anti-angiogenesis agents or inhibitors (e.g., angiostatin, retinoic acids and paclitaxel, estradiol derivatives, thiazolopyrimidine derivatives, etc.), apoptosis-inducing agents (e.g., antisense nucleotides that block oncogenes which inhibit apoptosis, tumor suppressors, TRAIL, TRAIL polypeptide, Fas-associated factor 1, interleukin-1β-converting enzyme, phosphotyrosine inhibitors, RXR retinoid receptor agonists, carbostyril derivatives, etc.), chelators (penicillamine, zinc, trientine, etc.) and other anti-obesity agents.

5.10 Therapeutic Kits

Therapeutic kits comprising the compounds of structural Formula (I) and/or pharmaceutical compositions thereof are also provided herein. The therapeutic kits may also contain other compounds (e.g., chemotherapeutic agents, natural products, hormones or antagonists, anti-angiogenesis agents or inhibitors, apoptosis-inducing agents or chelators) and/or pharmaceutical compositions thereof.

Therapeutic kits may have a single container which contains the compound of structural Formula (I) and/or pharmaceutical compositions thereof with or without other components (e.g., other compounds and/or pharmaceutical compositions thereof) or may have distinct container for each component. Preferably, therapeutic kits include a compound of structural Formula (I) and/or a pharmaceutical composition thereof packaged for use in combination with the co-administration of a second compound (preferably, a chemotherapeutic agent, a natural product, a hormone or antagonist, a anti-angiogenesis agent or inhibitor, an apoptosis-inducing agent or a chelator) or a pharmaceutical composition thereof. The components of the kit may be pre-complexed or each component may be in a separate distinct container prior to administration to a patient.

The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid.

Preferably, a therapeutic kit will contain apparatus (e.g., one or more needles, syringes, eye droppers, pipette, etc.), which enables administration of the components of the kit.

6. EXAMPLES

The invention is further defined by reference to the following examples, which describe in detail, preparation of compounds of the invention and methods for assaying for biological activity. It will be apparent to those skilled in the art that many modifications, both to materials and methods, may be practiced without departing from the scope of the invention.

6.1 Example 1

General Procedure for Synthesis of Tetrathiotungstate Derivatives

The quaternary ammonium hydroxide (2 eq.), as a commercially-available aqueous solution, was added to ammonium tetrathiotungstate (1 eq.) and deionized water was added until all the solid material was dissolved. The solution was placed on a rotary evaporator under vacuum (ca. 5-10 torr) with the bath at 20° C. for one hour and the water was replaced as needed to maintain a constant volume. The reaction mixture was then allowed to evaporate to dryness and the resulting yellow solid was recrystallized from deionized water and isopropanol. The solid was collected by filtration, washed with isopropanol and diethyl ether, and then dried under high vacuum for 24 hours in a vacuum desiccator in the presence of $P_2O_5$.

6.2 Example 2

General Procedure for Synthesis of Tetrathiotungstate Derivatives

The quaternary ammonium halide (2 eq.) as a solid was added to a suspension of ammonium tetrathiotungstate (1 eq.) in dry acetonitrile (5 mL per mmol of tetrathiotungstate) and the resulting mixture was stirred at room temperature under nitrogen for 18 hours. If this procedure resulted in a precipitate, the solid was collected by filtration, washed with isopropanol and diethyl ether and was recrystallized from deionized water and isopropanol. The yellow crystals were collected by filtration, washed with isopropanol and diethyl ether and dried under high vacuum for 24 hours in a vacuum desiccator in the presence of $P_2O_5$. If the solution remained clear, the solvent was removed in vacuo, the residue was taken up in dichloromethane, washed three times with water, once with brine, dried ($Na_2SO_4$), and the solution was concentrated. The resulting oil or solid was dried under high vacuum for 24 hours in a vacuum desiccator in the presence of $P_2O_5$.

6.3 Example 3

General Procedure for Synthesis of Tetrathiotungstate Derivatives

The quaternary ammonium halide (2 eq.) as a solution in deionized water (10 mL per mmol of tetrathiotungstate) was added to a suspension of ammonium tetrathiotungstate (1 eq.) in dry acetonitrile (20 mL per mmol of tetrathiotungstate) and the resulting mixture was stirred at room temperature for 18 hours. If this procedure resulted in a precipitate, the solid was collected by filtration, washed with water, isopropanol and diethyl ether, and then dried under high vacuum for 24 hours in a vacuum desiccator in the presence of $P_2O_5$. If the solution remained clear, the reaction mixture was first filtered, and the filtrate was concentrated in vacuo. The resulting solid was recrystallized from deionized water and isopropanol, the yellow crystals collected by filtration, washed with isopropanol and diethyl ether and then dried under high vacuum for 24 hours in a vacuum desiccator in the presence of $P_2O_5$.

6.4 Example 4

Tetrathiotungstate, bis(choline)

This compound was prepared from ammonium tetrathiotungstate (158 mg, 0.454 mmol) and a 50% by weight aqueous solution of choline hydroxide (222 mg, 0.916 mmol) according to the procedure of Example 1, which afforded 151 mg (64%) of the title compound as bright yellow crystals: IR (KBr, cm-1) 3402, 459; $^1$H NMR (300 MHz, DMSO-d6)δ 5.21 (t, J=4.8 Hz, 2H), 3.88-3.81 (m, 4H), 3.46-3.43 (m, 4H), 3.14 (s, 18H); $^{13}$C NMR (75 MHz, DMSO-d6) δ66.8 (2C), 55.2 (2C), 53.1 (6C); ES MS m/z (choline)$^+$104.3; UV ($H_2O$) 393.5 nm (ε=16730). Anal. Calcd for $C_{10}H_{28}N_2O_2S_4W$: C, 23.08; H, 5.42; N, 5.38; S, 24.65. Found: C, 23.17; H, 5.28; N, 5.43; S, 24.87.

6.5 Example 5

Tetrathiotungstate, bis(triethylmethyl ammonium)

This compound was prepared from ammonium tetrathiotungstate (164 mg, 0.471 mmol) and a 20% by weight aqueous solution of triethylmethylammonium hydroxide (627 mg, 0.941 mmol) according to the procedure of Example 1, which provided 147 mg (61%) of the title compound as bright yellow crystals: IR (KBr, cm-1) 460; $^1$H NMR (300 MHz, DMSO-d6) δ 3.29 (q, J=6.9 Hz, 12H), 2.91 (s, 6H), 1.21 (t, J=6.9 Hz, 18H); $^{13}$C NMR (75 MHz, DMSO-d6) δ 55.0 (6C), 46.0 (2C), 7.5 (6C); ES MS m/z (triethylmethyl ammonium)$^+$ 116.4; WV ($H_2O$) 393.5 nm (ε=16730). Anal. Calcd for $C_{14}H_{36}N_2S_4W$: C, 30.88; H, 6.66; N, 5.14; S, 23.55. Found: C, 30.87; H, 6.33; N, 5.18; S, 23.77.

6.6 Example 6

Tetrathiotungstate, bis(triethylphenyl ammonium)

This compound was prepared from ammonium tetrathiotungstate (155 mg, 0.444 mmol) and a 10% by weight aqueous solution of triethylphenylammonium hydroxide (1.74 g, 0.889 mmol) according to the procedure of Example 1, which provided 198 mg (69%) of the title compound as bright yellow crystals: IR (KBr, cm-1) 455; $^1$H NMR (300 MHz, DMSO-d6) δ 7.92 (d, J=8.4 Hz, 4H), 7.71-7.57 (m, 6H), 3.91 (q, J=7.1 Hz, 12H), 1.06 (t, J=7.1 Hz, 18H); $^{13}$C NMR (75 MHz, DMSO-d6) δ 141.7 (2C), 130.4 (4C), 130.0 (2C), 122.6 (4C), 55.3 (6C), 7.8 (6C); ES MS m/z (triethylphenyl ammonium)$^+$178.4; UV (H$_2$O) 393.5 nm (ε=15600). Anal. Calcd for $C_{24}H_{40}N_2S_4W$: C, 43.11; H, 6.03; N, 4.19; S, 19.18. Found: C, 42.99; H, 5.73; N, 4.25; S, 19.31.

6.7 Example 7

Tetrathiotungstate, bis(1,4-dimethylpyridinium)

This compound was prepared from ammonium tetrathiotungstate (163 mg, 0.467 mmol) and 1,4-dimethylpyridinium iodide (221 mg, 0.940 mmol) according to the procedure of Example 2, which provided 143 mg (58%) of the title compound as bright yellow crystals: IR (KBr, cm-1) 458; $^1$H NMR (300 MHz, DMSO-d6) δ 8.88 (d, J=6.4 Hz, 4H), 7.96 (d, J=6.4 Hz, 4H), 4.32 (s, 6H), 2.60 (s, 6H); $^{13}$C NMR (75 MHz, DMSO-d6) δ 158.1 (2C), 144.8 (4C), 128.0 (4C), 47.1 (2C), 21.4 (2C); ES MS m/z (1,4-dimethylpyridinium)$^+$ 108.3; UV (H$_2$O) 393.5 nm (ε=16030). Anal. Calcd for $C_{14}H_{20}N_2S_4W$: C, 31.82; H, 3.81; N, 5.30; S, 24.27. Found: C, 31.67; H, 3.77; N, 5.32; S, 24.13.

6.8 Example 8

Tetrathiotungstate, bis(1,1-dimethylpyrrolidinium)

This compound was prepared from ammonium tetrathiotungstate (300 mg, 0.861 mmol) and 1,1-dimethylpyrrolidinium iodide (400 mg, 1.76 mmol) according to the procedure of Example 3, which provided 223 mg (51%) of the title compound as bright yellow crystals: IR (KBr, cm-1) 455; $^1$H NMR (300 MHz, DMSO-d6) δ 3.53-3.47 (m, 8H), 3.13 (s, 12H), 2.14-2.08 (m, 8H); $^{13}$C NMR (75 MHz, DMSO-d6) δ 64.8 (4C), 51.0 (4C), 21.5 (4C); ES MS m/z (1,1-dimethylpyrrolidinium)$^+$100.3; UV (H$_2$O) 393.5 nm (ε=16950). Anal. Calcd for $C_{12}H_{28}N_2S_4W$: C, 28.12; H, 5.51; N, 5.47; S, 25.03. Found: C, 27.90; H, 5.47; N, 5.56; S, 25.01.

6.9 Example 9

Tetrathiotungstate, bis(trimethylphenylammonium)

This compound was prepared from ammonium tetrathiotungstate (167 mg, 0.479 mmol) and phenyltrimethyl-ammonium chloride (166 mg, 0.968 mmol) according to the procedure of Example 2, which provided 139 mg (50%) of the title compound as bright yellow crystals: IR (KBr, cm-1) 459; $^1$H NMR (300 MHz, DMSO-d6) δ 7.99 (d, J=8.2 Hz, 4H), 7.68-7.55 (m, 6H), 3.64 (s, 18H); $^{13}$C NMR (75 MHz, DMSO-d6) δ 147.3 (2C), 130.1 (4C), 130.0 (2C), 120.5 (4C), 56.4 (6C); ES MS m/z (trimethylphenylammonium)+136.2; UV (H$_2$O) 394.0 nm (ε=15630). Anal. Calcd for $C_{18}H_{28}N_2S_4W$: C, 36.99; H, 4.83; N, 4.79; S, 21.94. Found: C, 36.88; H, 4.72; N, 4.90; S, 21.92.

6.10 Example 10

Tetrathiotungstate, bis(acetylcholine)

This compound was prepared from ammonium tetrathiotungstate (171 mg, 0.491 mmol) and acetylcholine chloride (179 mg, 0.987 mmol) according to the procedure of Example 2, which provided 163 mg (55%) of the title compound as bright yellow crystals: IR (KBr, cm-1) 1749,1729, 473, 456; $^1$H NMR (300 MHz, DMSO-d6) δ 4.47-4.41 (m, 4H), 3.72-3.69 (m, 4H), 3.16 (s, 18H), 2.07 (s, 6H); $^{13}$C NMR (75 MHz, DMSO-d6) δ 169.9 (2C), 63.8 (2C), 57.9 (2C), 53.0 (6C), 20.7 (2C); ES MS m/z (acetylcholine)$^+$146.4; UV (H$_2$O) 393.5 nm (ε=15400). Anal. Calcd for $C_{14}H_{32}N_2O_4S_4W$: C, 27.82; H, 5.34; N, 4.63; S, 21.22. Found: C, 27.62; H 5.12; N, 4.68; S, 20.71.

6.11 Example 11

Tetrathiotungstate, bis[alkyldimethyl(phenylmethyl) ammonium]

This compound was prepared from ammonium tetrathiotungstate (320 mg, 0.920 mmol) and benzalkonium chloride (664 mg, 1.84 mmol) according to the procedure of Example 2, which afforded 651 mg (74%) of the title compound as a thick, red oil: IR (film, cm-1) 466; $^1$H NMR (300 MHz, DMSO-d6) δ 7.59-7.48 (m, 10H), 4.56 (s, 4H), 3.31-3.23 (in, 4H), 2.97 (s, 12H), 1.84-1.72 (m, 4H), 1.32-1.22 (m, 40H), 0.88-0.82 (m, 6H); ES MS m/z [dodecyldimethyl(phenylmethyl) ammonium]$^+$304.7, [tetradecyldimethyl(phenylmethyl) ammonium]$^+$332.7; UV (DMSO) 399.0 nm (ε=10400).

6.12 Example 12

Tetrathiotungstate, suberyldicholine

This compound was prepared from ammonium tetrathiotungstate (299 mg, 0.860 mmol) and suberyldicholine diiodide (516 mg, 0.860 mmol) according to the procedure of Example 2, which afforded 115 mg (20%) of the title compound as bright yellow crystals: IR (KBr, cm-1) 1733, 1719, 455; $^1$H NMR (300 MHz, DMSO-d6) δ 4.48-4.42 (m, 4H), 3.73-3.69 (m, 4H), 3.17 (s, 18H), 2.35 (t, J=7.4 Hz, 4H), 1.59-1.48 (m, 4H), 1.32-1.26 (m, 4H); $^{13}$C NMR (75 MHz, DMSO-d6) δ 172.3 (2C), 63.7 (2C), 57.7 (2C), 52.8 (6C), 33.2 (2C), 28.0 (2C), 23.9 (2C); UV (H$_2$O) 394.0 nm (ε=15570)

6.13 Example 13

Tetrathiotungstate, pentane-1,5-bis(trimethylammonium)

This compound was prepared from ammonium tetrathiotungstate (140 mg, 0.402 mmol) and N,N-pentamethylenebis (trimethylammonium iodide) (195 mg, 0.442 mmol) according to the procedure of Example 3, which afforded 109 mg (54%) of the title compound as a bright yellow powder: IR (KBr, cm-1) 456; $^1$H NMR (300 MHz, D$_2$O) δ 3.34-3.26 (m, 4H), 3.07 (s, 18H), 1.89-1.77 (m, 4H), 1.45-1.34 (m, 2H); UV (H$_2$O) 394.0 nm (ε=15950). Anal. Calcd for $C_{11}H_{28}N_2S_4W$: C, 26.40; H, 5.64; N, 5.60; S, 25.63. Found: C, 26.60; H, 5.26; N, 5.75; S, 24.64.

6.14 Example 14

Tetrathiotungstate, butane-1,4-bis(trimethylammonium)

This compound was prepared from ammonium tetrathiotungstate (200 mg, 0.574 mmol) and N,N-tetramethylenebis (trimethylarnmonium iodide) (271 mg, 0.632 mmol) according to the procedure of Example 3 and afforded 185 mg (66%)

of the title compound as a bright yellow powder: IR (KBr, cm-1) 456; $^1$H NMR (300 MHz, D$_2$O) δ 3.45-3.35 (m, 4H), 3.11 (s, 18H), 1.92-1.82 (m, 4H); UV (H20) 394.0 nm (ε=15990). Anal. Calcd for C$_{10}$H$_{26}$N$_2$S$_4$W: C, 24.69; H, 5.39; N, 5.76; S, 26.37. Found: C, 24.77; H, 5.35; N, 5.85; S, 25.80.

6.15 Example 15

Tetrathiotungstate, propane-1,3-bis(trimethylammonium)

This compound was prepared from ammonium tetrathiotungstate (201 mg, 0.578 mmol) and N,N-trimethylenebis(trimethylammonium iodide) (263 mg, 0.635 mmol) according to the procedure of Example 3, and afforded 192 mg (70%) of the title compound as a bright yellow powder: IR (KBr, cm-1) 456; UV (H$_2$O) 393.5 nm (ε=16190). Anal. Calcd for C$_9$H$_{24}$N$_2$S$_4$W: C, 22.88; H, 5.12; N, 5.93; S, 27.15. Found: C, 22.94; H, 5.01; N, 6.01; S, 26.79.

6.16 Example 15

Tetrathiotungstate, ethylenebis(trimethylammonium)

This compound was prepared from ammonium tetrathiotungstate (200 mg, 0.573 mmol) and ethylenebis(trimethylammonium iodide) (249 mg, 0.623 mmol) according to the procedure of Example 3, and afforded 171 mg (65%) of the title compound as a bright yellow powder: IR (KBr, cm-1) 459; UV (H20) 393.5 nm (ε=15720). Anal. Calcd for C$_8$H$_{22}$N$_2$S$_4$W: C, 20.96; H, 4.84; N, 6.11; S, 27.98. Found: C, 20.88; H, 4.71; N, 6.21; S, 27.39.

6.17 Example 17

Tetrathiotungstate, bis(N-benzyl-2-phenylethyl ammonium)

This compound was prepared from ammonium tetrathiotungstate (295 mg, 0.848 mmol) and N-benzyl-2-phenylethylammonium chloride (422 mg, 1.70 mmol) according to the procedure of Example 3, but with the addition of 6 mL of deionized water, and afforded 317 mg (51%) of the title compound as an orange solid: IR (KBr, cm-1) 455; $^1$H NMR (300 MHz, DMSO-d6) δ 8.83 (br s, 4H), 7.57-7.52 (m, 4H), 7.48-7.40 (m, 6H), 7.36-7.23 (m, 10H), 4.22 (s, 4H), 3.21-3.15 (m, 4H), 3.03-2.95 (m, 4H); $^{13}$C NMR (75 MHz, DMSO-d6) δ 137.4 (2C), 132.5 (2C), 130.0 (4C), 128.9 (2C), 128.72 (8C), 128.68 (4C), 126.8 (2C), 50.6 (2C), 48.1 (2C), 31.8 (2C); ES MS m/z [N-benzyl-2-phenylethyl ammonium]$^+$212.4; UV (DMSO) 399.5 nm (ε=16270).

6.18 Example 18

Tetrathiotungstate, bis(1-ethyl-3-methyl-1H-imidazolium)

This compound was prepared from tetrathiotungstate, bis(ammonium) (0.400 g, 1.15 mmol) and 1-ethyl-3-methyl-1H-imidazolium chloride (0.354 g, 2.41 mmol) according to the procedure of Example 3 giving the title compound (0.217 g, 35%) as a bright yellow solid: IR (KBr pellet, cm$^{-1}$) 3438, 3068, 1569, 1560, 1169, 450; $^1$H NMR (300 MHz, DMSO-d6) δ 9.22 (s, 1H), 7.78 (s, 1H), 7.70 (s, 1H), 4.21 (q, 2 H, J=7.3 Hz), 3.31 (s, 3H), 1.42 (t, 3 H, J=7.3 Hz); $^{13}$C NMR (75 MHz, DMSO-d$_6$) δ 136.4, 123.4, 121.8, 44.0, 35.6, 15.1; MS m/z (C$_6$H$_{11}$N$_2$)$^+$111.3; UV (H$_2$O) 394 nm (ε=15,891); Anal. calcd for C$_{12}$H$_{22}$N$_4$WS$_4$: C, 26.97; H, 4.15; N, 10.48; S, 24.00. Found: C, 26.91, H, 3.92, N, 10.55; S, 23.67.

6.19 Example 19

Tetrathiotungstate, bis(benzzyltrimethylammonium)

This compound was prepared from tetrathiotungstate, bis(ammonium) (0.200 g, 0.574 mmol) and benzyltrimethylammonium hydroxide (0.48 g of a 40% aqueous solution, 1.15 mmol) according to the procedure of Example 1 to provide giving the title compound (0.246 g, 70%) as a bright yellow solid: IR (KBr pellet, cm$^{-1}$) 3446, 2999, 1456, 458; $^1$H NMR (300 MHz, DMSO-d$_6$) δ 7.53-7.55 (m, 10H), 4.56 (s, 4 H), 3.05 (s, 18H); $^{13}$C NMR (75 MHz, DMSO-d$_6$) δ 132.7, 130.2, 128.8, 128.3, 67.7, 51.7 (t); MS m/z (C$_{10}$H$_{16}$N)$^+$150.3; UV (H$_2$O) 394 nm (ε=15,027); Anal. calcd for C$_{20}$H$_{32}$N$_2$WS$_4$: C, 39.21; H, 5.27; N, 4.57; S, 20.94. Found: C, 39.28, H, 4.88, N, 4.65; S, 20.89.

6.20 Example 20

Tetrathiotungstate, bis(2-hydroxyiminomethyl-1-methyl-pyridinium)

This compound was prepared from tetrathiotungstate, bis(ammonium) (0.200 g, 0.574 mmol) and 2-pyridinealdoxime methochloride (0.198 g, 1.15 mmol) according to the procedure of Example 3 to give the title compound (0.198 g, 59%) as a bright yellow solid: IR (KBr pellet, cm$^{-1}$) 3077, 1508, 1005, 455; $^1$H NMR (300 MHz, DMSO-d$_6$) δ 9.04 (d, 1 H, J=5.9 Hz), 8.68 (s, 1H), 8.55 (app t, 1H), 8.37 (d, 1 H, J=8.0 Hz), 8.07 (app t, 1H), 4.39 (s, 3H); $^{13}$C NMR (75 MHz, DMSO-d$_6$) δ 147.3, 146.7, 144.8, 141.7, 127.1, 124.7, 46.1; MS m/z (C$_7$H$_9$N$_2$O)$^+$137.2; V (H$_2$O) 394 nm (ε=15380); Anal. calcd for C$_{14}$H$_{18}$N$_4$O$_2$WS$_4$: C, 28.67; H, 3.09; N, 9.55; S, 21.87. Found: C, 28.51, H, 2.87, N, 9.63; S, 21.55.

6.21 Example 21

Tetrathiotungstate, bis(acetyl-β-methylcholine)

This compound was prepared from tetrathiotungstate, bis(ammonium) (0.200 g, 0.574 mmol) and acetyl-p-methylcholine chloride (0.235 g, 1.20 mmol) according to the procedure of Example 3 giving the title compound (0.115 g, 32%) as a bright yellow solid: IR (KBr pellet, cm$^{-1}$) 3452, 3008, 1735, 1252, 454; $^1$H NMR (300 MHz, DMSO-d$_6$) δ 5.27 (m, 1H), 3.58-3.74 (m, 2H), 3.13 (s, 9H), 2.06 (s, 3H), 1.24 (d, 3 H, J=6.3 Hz); $^{13}$C NMR (75 MHz, DMSO-d$_6$) δ 169.5, 67.6, 65.2, 53.2, 21.1, 18.5; MS m/z (C$_8$H$_{18}$NO$_2$)$^+$160.3; UV (H20) 394 nm (ε=15831); Anal. calcd for C$_{16}$H$_{36}$N$_2$O$_4$S$_4$W: C, 30.38; H, 5.74; N, 4.43; S, 20.28. Found: C, 30.10, H, 5.62, N, 4.47; S, 20.47.

6.22 Example 22

Tetrathiotungstate, (succinylcholine)

This compound was prepared from tetrathiotungstate, bis(ammonium) (0.400 g, 1.15 mmol) and succinylcholine chloride dihydrate (0.456 g, 1.15 mmol) according to the procedure of Example 3 to give the title compound (0.414 g, 60%) as a bright yellow solid: IR (KBr pellet, cm$^{-1}$) 3005, 1732, 1208, 1150, 455; $^1$H NMR (300 MHz, DMSO-d$_6$) δ 4.47 (m, 4H), 3.68-3.72 (m, 4H), 3.30 (d, 18 H, J=4.2 Hz), 2.66 (m, 4 H); $^{13}$C NMR (75 MHz, DMSO-d$_6$) δ 171.3, 58.0, 52.9, 28.4;

UV (H$_2$O) 394 nm (ε=15513); Anal. calcd for C$_{14}$H$_{30}$N$_2$O$_4$S$_4$W: C, 27.91; H, 5.02; N, 4.65; S, 21.29. Found: C, 27.84, H, 4.80, N, 4.66; S, 21.06.

6.23 Example 23

Tetrathiotungstate, (ethylene-1,2-bisammonium)

This compound was prepared from tetrathiotungstate, bis(ammonium) (0.300 g, 0.862 mmol), ammonium chloride (0.092 g, 1.72 mmol) and ethylenediamine (57.6 μl, 0.862 mmol) according to the procedure of Example 3 to give the title compound (0.257 g, 80%) as a bright yellow solid: IR (KBr pellet, cm$^{-1}$) 3002, 1435, 1025, 45 1; $^1$H NMR (300 MHz, DMSO-d$_6$) δ 7.89 (bs, 6H), 3.09 (s, 4H); $^{13}$C NMR (75 MHz, DMSO-d$_6$) δ 36.8; UV (H$_2$O) 394 nm (ε=13291); Anal. calcd for C$_2$H$_{10}$N$_2$S$_4$W: C, 6.42; H, 2.69; N, 7.49; S, 34.27. Found: C, 6.58, H, 2.43, N, 7.49; S, 32.98.

6.24 Example 24

Moisture Stability of Tetrathiotungstate Salts

Salts of tetrathiotungstate were placed in an acrylic chamber at room temperature with 95% relative humidity for two weeks. The samples were analyzed for purity according to the previously reported method with the exception that the absorbance was monitored at 493 nm and the molar absorptivity was 15710 M$^{-1}$ cm$^{-1}$ (McDonald et. al., *Inorg. Chim. Acta* 1983, 72, 205-210). The results are reported below in Table 1

TABLE 1

| Name | % degradation |
| --- | --- |
| Tetrathiotungstate, bis(triethylphenyl ammonium) | −0.12 |
| Tetrathiotungstate, bis(ammonium) | −0.46 |
| Tetrathiotungstate, bis(trimethylphenylammonium) | −0.46 |
| Tetrathiotungstate, bis(benzyltrimethylammonium) | 0.41 |
| Tetrathiotungstate, bis(acetylcholine) | 2.4 |
| Tetrathiotungstate, bis(choline) | 3.0 |
| Tetrathiotungstate, bis(1-ethyl-3-methyl-1H-imidazolium) | 1.3 |
| Tetrathiotungstate, bis(1,4-dimethylpyridinium) | 2.0 |
| Tetrathiotungstate, bis(acetyl-β-methylcholine) | 4.2 |
| Tetrathiotungstate, bis(1,1-dimethylpyrrolidinium) | 0.04 |
| Tetrathiotungstate, bis(2-hydroxyiminomethyl-1-methyl-pyridinium) | 5.6 |
| Tetrathiotungstate, pentane-1,5-bis(trimethylammonium) | 19.8* |
| Tetrathiotungstate, ethylenebis(trimethylammonium) | 8.6* |
| Tetrathiotungstate, propane-1,3-bis(trimethylammonium) | 23.8* |
| Tetrathiotungstate, butane-1,4-bis(trimethylammonium) | 5.7* |
| Tetrathiotungstate, (succinylcholine) | 23.3* |
| Tetrathiotungstate, suberyldicholine | 18.4* |
| Tetrathiomolybdate, bis(ammonium) | 56‡ ± 5 |
| Tetrathiomolybdate, bis(choline) | 36‡ ± 2 |

*partially soluble
‡average of 2 data points

6.25 Example 25

Copper-Binding Ability of Tetrathiotungstate Salts

The copper-binding ability of tetrathiotungstate salts was determined according to the ability of tetrathiotungstate salts to inhibit cysteine autooxidation as reported in Table 2 below.

TABLE 2

Inhibition of Cysteine Autooxidation (100 μM Cys, 100 μM coumarin-3-carboxylic acid, 100 μM CuSO$_4$)

| inhibitor | inhibitor concentration | % inhibition |
| --- | --- | --- |
| trientine | 50 μM | 39.71% |
| Tetrathiotungstate, bis(ammonium) | 50 μM | 95.94% |
| Tetrathiotungstate, bis(triethylphenyl ammonium) | 50 μM | 91.32% |
| Tetrathiotungstate, bis(trimethylphenylammonium) | 50 μM | 91.53% |
| Tetrathiotungstate, bis(benzyltrimethylammonium) | 50 μM | 94.62% |
| Tetrathiotungstate, bis(acetylcholine) | 50 μM | 90.36% |
| Tetrathiotungstate, bis(choline) | 50 μM | 92.54% |
| Tetrathiotungstate, bis(1-ethyl-3-methyl-1H-imidazolium) | 50 μM | 91.16% |
| Tetrathiotungstate, bis(1,4-dimethylpyridinium) | 50 μM | 89.98% |
| Tetrathiotungstate, bis(acetyl-β-methylcholine) | 50 μM | 90.40% |
| Tetrathiotungstate, bis(1,4-dimethylpyridinium) | 50 μM | 89.66% |
| Tetrathiotungstate, bis(2-hydroxyiminomethyl-1-methyl-pyridinium) | 50 μM | 91.15% |
| Tetrathiotungstate, pentane-1,5-bis(trimethylammonium) | 50 μM | 90.69% |
| Tetrathiotungstate, bis(choline) | 50 μM | 91.99% |
| Tetrathiomolybdate, bis(ammonium) | 50 μM | 94.24% |
| Tetrathiotungstate, ethylenebis(trimethylammonium) | 50 μM | 89.60% |
| Tetrathiotungstate, propane-1,3-bis(trimethylammonium) | 50 μM | 92.95% |
| Tetrathiotungstate, butane-1,4-bis(trimethylammonium) | 50 μM | 91.75% |
| trientine | 10 μM | 4.27% |
| Tetrathiomolybdate, bis(ammonium) | 10 μM | 87.71% |
| Tetrathiotungstate, ethylenebis(trimethylammonium) | 10 μM | 84.66% |
| Tetrathiotungstate, propane-1,3-bis(trimethylammonium) | 10 μM | 85.53% |
| Tetrathiotungstate, butane-1,4-bis(trimethylammonium) | 10 μM | 87.32% |
| trientine | 10 μM | 17.72% |
| Tetrathiomolybdate, bis(ammonium) | 10 μM | 76.69% |
| Tetrathiotungstate, (succinylcholine) | 10 μM | 81.38% |
| Tetrathiotungstate, suberyldicholine | 10 μM | 77.83% |
| trientine | 1 μM | 0.00% |
| Tetrathiomolybdate, bis(ammonium) | 1 μM | 68.48% |
| Tetrathiotungstate, (succinylcholine) | 1 μM | 66.06% |
| Tetrathiotungstate, suberyldicholine | 1 μM | 67.74% |

6.25 Example 25

Inhibition of Angiogenesis in Matrigel® Plug Assay by Ammonium Tetrathiotungstate Ammonium tetrathiotungstate was assayed in the Matrigel® plug assay as described in Section 5.4.7, supra. Two positive controls were used with positive control 1 measured five days after implantation when treatment began and negative control 2 measured five days after implantation when treatment ended. Two negative controls were used with negative control 1 measured five days after implantation when treatment began and negative control 2 measured five days after implantation when treatment ended. As can be seen in FIG. 1, treatment with ammonium tetrathiotungstate resulted in about 34% inhibition using this assay.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated by reference in their entirety.

What is claimed is:

1. A compound of structural formula (I):

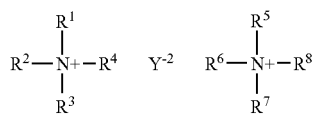

or a solvate or hydrate thereof,
wherein:
$R^1(R^2)(R^3)(R^4)N$ has the structure:

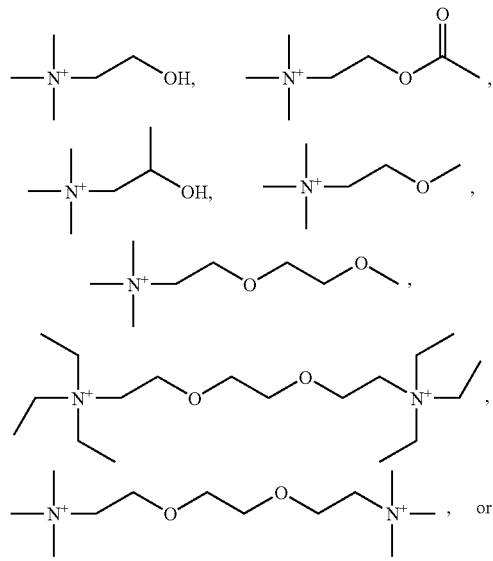

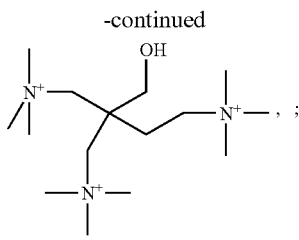

$R^5$, $R^6$, and $R^7$, and $R^8$ are independently hydrogen, alkyl, substituted alkyl, cycloalkyl, substituted cycloalkyl, heteroalkyl or substituted heteroalkyl; and $Y^{-2}$ is $(W_2S_{12})^{-2}$, $(W_2S_9)^{-2}$, $(W_2S_7)^{-2}$, $(W_2S_8)^{-2}$, $(W_2S_{11})^{-2}$, $(W_2S_6)^{-2}$ or $(W_2S_{13})^{-2}$.

2. A compound of structural formula (I):

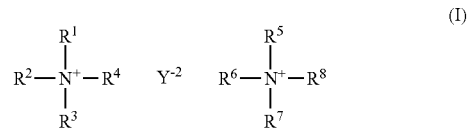

or a solvate or hydrate thereof
wherein:
$Y^{-2}$ is $(WS_4)^{-2}$;
wherein $R^1(R^2)(R^3)(R^4)N$ has the structure:

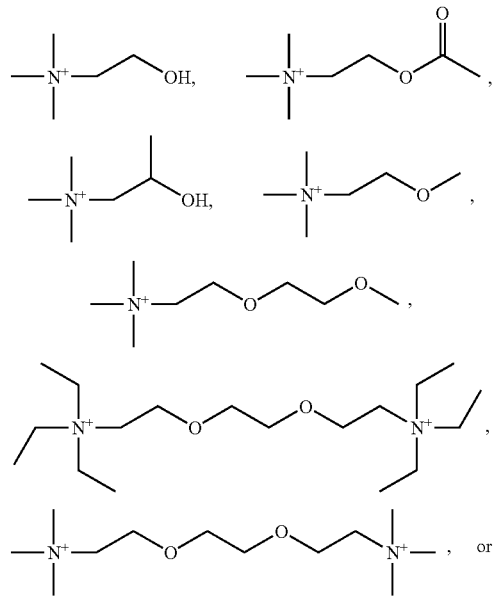

and
wherein $R^5$, $R^6$, and $R^7$, and $R^8$ are independently hydrogen, alkyl, substituted alkyl, cycloalkyl, substituted cycloalkyl, heteroalkyl or substituted heteroalkyl.

3. The compound of claim 2, wherein $R^1(R^2)(R^3)(R^4)N=R^5)(R^6)(R^7)(R^8)N$.

4. The compound of claim 2, wherein $R^1(R^2)(R^3)(R^4)N$ has the structure:

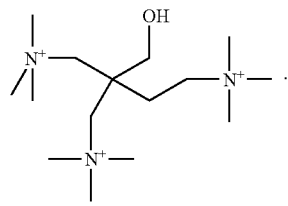

5. A pharmaceutical composition comprising a compound of structural formula (I):

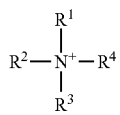 $Y^{-2}$ 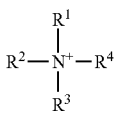 (I)

or a solvate or hydrate thereof,
wherein:
$Y^{-2}$ is $(WS_4)^{-2}$;
$R^1(R^2)(R^3)(R^4)N$ has the structure:

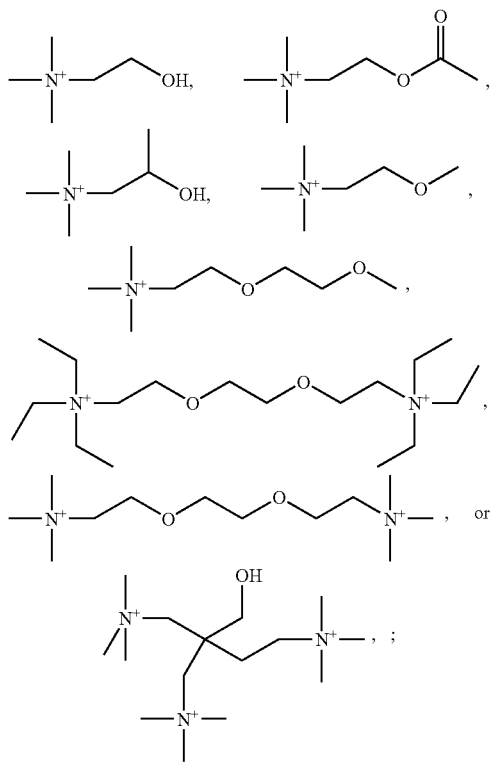

and $R^5$, $R^6$, and $R^7$, and $R^8$ are independently hydrogen, alkyl, substituted alkyl, cycloalkyl, substituted cycloalkyl, heteroalkyl or substituted heteroalkyl;
and a pharmaceutically acceptable diluent, excipient or adjuvant.

6. The compound of claim 2,
wherein $R^1(R^2)(R^3)(R^4)N$ has the structure:

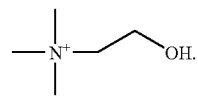

7. A pharmaceutical composition comprising a compound of structural formula (I):

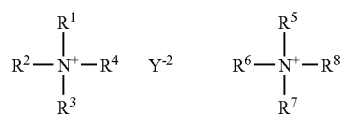

or a solvate or hydrate thereof,
wherein $Y^{-2}$ is $(WS_4)^{-2}$; and
wherein $R^1(R^2)(R^3)(R^4)N$ has the structure:

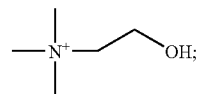

and wherein $R^5$, $R^6$ and $R^7$ and $R^8$ are independently hydrogen, alkyl, substituted alkyl, cycloalkyl, substituted cycloalkyl, heteroalkyl or substituted heteroalkyl
and a pharmaceutically acceptable diluent, excipient or adjuvant.

8. The compound of claim 6, wherein $R^1(R^2)(R^3)(R^4)N = R^5(R^6)(R^7)(R^8)N$.

9. The pharmaceutical composition of claim 7, wherein $R^1(R^2)(R^3)(R^4)N = R^5(R^6)(R^7)(R^8)N$.

10. The compound of claim 1, wherein $R^1(R^2)(R^3)(R^4)N$ has the structure:

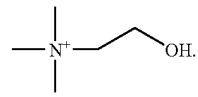

11. The compound of claim 10, wherein $R^1(R^2)(R^3)(R^4)N = R^5(R^6)(R^7)(R^8)N$.

12. A pharmaceutical composition comprising a compound of structural formula (I):

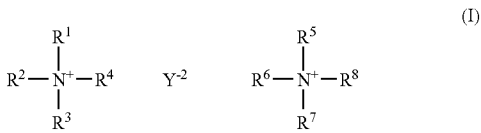 (I)

or a solvate or hydrate thereof wherein:
R$^1$(R$^2$)(R$^3$)(R$^4$)N has the structure:

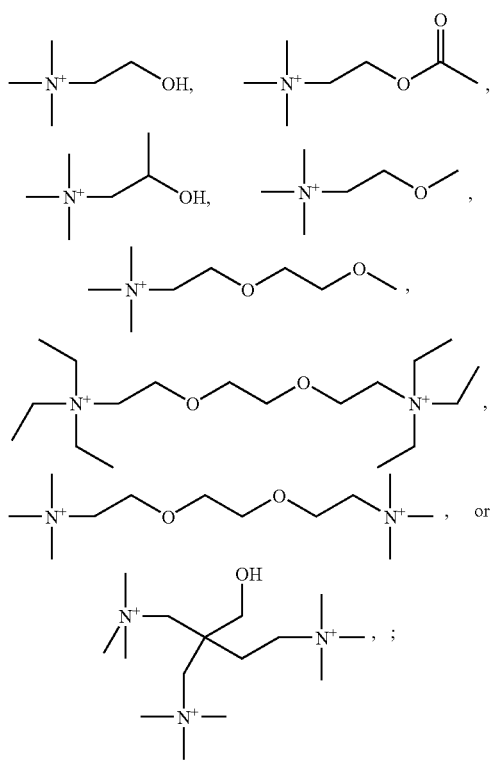

R$^5$, R$^6$, and R$^7$, and R$^8$ are independently hydrogen, alkyl, substituted alkyl, cycloalkyl, substituted cycloalkyl, heteroalkyl or substituted heteroalkyl; and Y$^{-2}$ is (W$_2$S$_{12}$)$^{-2}$, (W$_2$S$_9$)$^{-2}$, (W$_2$S$_7$)$^{-2}$, (W$_2$S$_8$)$^{-2}$, (W$_2$S$_{11}$)$^{-2}$, (W$_2$S$_6$)$^{-2}$ or (W$_2$S$_{13}$)$^{-2}$; and and a pharmaceutically acceptable diluent, excipient or adjuvant.

13. The pharmaceutical composition of claim 12, wherein R$^1$(R$^2$)(R$^3$)(R$^4$)N has the structure:

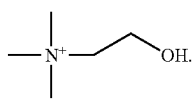

14. The pharmaceutical composition of claim 13, wherein R$^1$(R$^2$)(R$^3$)(R$^4$)N=R$^5$(R$^6$)(R$^7$)(R$^8$)N.

15. The compound of claim 1, wherein R$^1$(R$^2$)(R$^3$)(R$^4$)N=R$^5$(R$^6$)(R$^7$)(R$^8$)N.

* * * * *